(12) United States Patent
Braido

(10) Patent No.: US 10,945,836 B2
(45) Date of Patent: *Mar. 16, 2021

(54) SEALING STRUCTURES FOR PARAVALVULAR LEAK PROTECTION

(71) Applicant: St. Jude Medical, Cardiology Division, Inc., St. Paul, MN (US)

(72) Inventor: Peter N. Braido, Wyoming, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 85 days.

This patent is subject to a terminal disclaimer.

(21) Appl. No.: 15/892,988

(22) Filed: Feb. 9, 2018

(65) Prior Publication Data

US 2018/0168805 A1 Jun. 21, 2018

Related U.S. Application Data

(62) Division of application No. 14/547,595, filed on Nov. 19, 2014, now Pat. No. 9,889,004.

(60) Provisional application No. 61/906,076, filed on Nov. 19, 2013.

(51) Int. Cl.
*A61F 2/24* (2006.01)

(52) U.S. Cl.
CPC .... *A61F 2/2418* (2013.01); *A61F 2210/0014* (2013.01); *A61F 2220/0075* (2013.01); *A61F 2230/0013* (2013.01); *A61F 2230/0065* (2013.01); *A61F 2230/0091* (2013.01); *A61F 2250/0069* (2013.01)

(58) Field of Classification Search
CPC ............ A61F 2/2418; A61F 2220/0075; A61F 2/2412; A61F 2/2409; A61F 2250/0069; A61F 2/07; A61F 2/2427; A61F 2002/075
See application file for complete search history.

(56) References Cited

U.S. PATENT DOCUMENTS

| | | | |
|---|---|---|---|
| 3,657,744 | A | 4/1972 | Ersek |
| 4,275,469 | A | 6/1981 | Gabbay |
| 4,423,730 | A | 1/1984 | Gabbay |
| 4,491,986 | A | 1/1985 | Gabbay |
| 4,759,758 | A | 7/1988 | Gabbay |

(Continued)

FOREIGN PATENT DOCUMENTS

| | | |
|---|---|---|
| DE | 19857887 A1 | 7/2000 |
| DE | 10121210 A1 | 11/2002 |

(Continued)

OTHER PUBLICATIONS

International Search Report and Written Opinion for Application No. PCT/US2014/066284 dated Feb. 4, 2015.

(Continued)

*Primary Examiner* — Ann Schillinger
(74) *Attorney, Agent, or Firm* — Lerner, David, Littenberg, Krumholz & Mentlik, LLP

(57) ABSTRACT

A prosthetic heart valve for replacing a native valve includes a collapsible and expandable stent having a proximal end and a distal end, and a valve assembly disposed within the stent, the valve assembly including a plurality of leaflets and a cuff annularly disposed about the stent. The cuff includes a surplus portion capable of forming a sealing structure having a diameter greater than a diameter of the proximal end of the stent when deployed.

19 Claims, 23 Drawing Sheets

(56) References Cited

U.S. PATENT DOCUMENTS

| | | | |
|---|---|---|---|
| 4,816,029 A * | 3/1989 | Penny, III | A61F 2/2409 623/2.19 |
| 4,878,906 A | 11/1989 | Lindemann et al. | |
| 4,922,905 A | 5/1990 | Strecker | |
| 4,994,077 A | 2/1991 | Dobben | |
| 5,411,552 A | 5/1995 | Andersen et al. | |
| 5,415,664 A | 5/1995 | Pinchuk | |
| 5,480,423 A | 1/1996 | Ravenscroft et al. | |
| 5,843,167 A | 12/1998 | Dwyer et al. | |
| 5,855,601 A | 1/1999 | Bessler et al. | |
| 5,924,424 A | 7/1999 | Stevens et al. | |
| 5,935,163 A | 8/1999 | Gabbay | |
| 5,961,549 A | 10/1999 | Nguyen et al. | |
| 5,968,068 A | 10/1999 | Dehdashtian et al. | |
| 6,045,576 A | 4/2000 | Starr et al. | |
| 6,077,297 A | 6/2000 | Robinson et al. | |
| 6,083,257 A | 7/2000 | Taylor et al. | |
| 6,090,140 A | 7/2000 | Gabbay | |
| 6,214,036 B1 | 4/2001 | Letendre et al. | |
| 6,264,691 B1 | 7/2001 | Gabbay | |
| 6,267,783 B1 | 7/2001 | Letendre et al. | |
| 6,306,141 B1 | 10/2001 | Jervis | |
| 6,368,348 B1 | 4/2002 | Gabbay | |
| 6,419,695 B1 | 7/2002 | Gabbay | |
| 6,458,153 B1 | 10/2002 | Bailey et al. | |
| 6,468,660 B2 | 10/2002 | Ogle et al. | |
| 6,488,702 B1 | 12/2002 | Besselink | |
| 6,517,576 B2 | 2/2003 | Gabbay | |
| 6,533,810 B2 | 3/2003 | Hankh et al. | |
| 6,582,464 B2 | 6/2003 | Gabbay | |
| 6,610,088 B1 | 8/2003 | Gabbay | |
| 6,623,518 B2 | 9/2003 | Thompson et al. | |
| 6,652,578 B2 | 11/2003 | Bailey et al. | |
| 6,685,625 B2 | 2/2004 | Gabbay | |
| 6,716,244 B2 | 4/2004 | Klaco | |
| 6,719,789 B2 | 4/2004 | Cox | |
| 6,730,118 B2 | 5/2004 | Spenser et al. | |
| 6,783,556 B1 | 8/2004 | Gabbay | |
| 6,790,230 B2 | 9/2004 | Beyersdorf et al. | |
| 6,814,746 B2 | 11/2004 | Thompson et al. | |
| 6,830,584 B1 | 12/2004 | Seguin | |
| 6,869,444 B2 | 3/2005 | Gabbay | |
| 6,893,460 B2 | 5/2005 | Spenser et al. | |
| 6,908,481 B2 | 6/2005 | Cribier | |
| 6,951,573 B1 | 10/2005 | Dilling | |
| 7,018,406 B2 | 3/2006 | Seguin et al. | |
| 7,025,780 B2 | 4/2006 | Gabbay | |
| 7,137,184 B2 | 11/2006 | Schreck | |
| 7,160,322 B2 | 1/2007 | Gabbay | |
| 7,195,641 B2 | 3/2007 | Palmaz et al. | |
| 7,247,167 B2 | 7/2007 | Gabbay | |
| 7,267,686 B2 | 9/2007 | DiMatteo et al. | |
| 7,276,078 B2 | 10/2007 | Spenser et al. | |
| 7,311,730 B2 | 12/2007 | Gabbay | |
| 7,320,704 B2 * | 1/2008 | Lashinski | A61F 2/2409 623/2.11 |
| 7,329,278 B2 | 2/2008 | Seguin et al. | |
| 7,374,573 B2 | 5/2008 | Gabbay | |
| 7,381,218 B2 | 6/2008 | Schreck | |
| 7,381,219 B2 | 6/2008 | Salahieh et al. | |
| 7,452,371 B2 | 11/2008 | Pavcnik et al. | |
| 7,510,572 B2 | 3/2009 | Gabbay | |
| 7,510,575 B2 | 3/2009 | Spenser et al. | |
| 7,524,331 B2 | 4/2009 | Birdsall | |
| 7,534,261 B2 | 5/2009 | Friedman | |
| RE40,816 E | 6/2009 | Taylor et al. | |
| 7,585,321 B2 | 9/2009 | Cribier | |
| 7,628,805 B2 | 12/2009 | Spenser et al. | |
| 7,682,390 B2 | 3/2010 | Seguin | |
| 7,708,775 B2 | 5/2010 | Rowe et al. | |
| 7,731,742 B2 | 6/2010 | Schlick et al. | |
| 7,748,389 B2 | 7/2010 | Salahieh et al. | |
| 7,780,725 B2 | 8/2010 | Haug et al. | |
| 7,799,069 B2 | 9/2010 | Bailey et al. | |
| 7,803,185 B2 | 9/2010 | Gabbay | |
| 7,824,442 B2 | 11/2010 | Salahieh et al. | |
| 7,837,727 B2 | 11/2010 | Goetz et al. | |
| 7,846,203 B2 | 12/2010 | Cribier | |
| 7,846,204 B2 | 12/2010 | Letac et al. | |
| 7,857,845 B2 | 12/2010 | Stacchino et al. | |
| 7,892,281 B2 | 2/2011 | Seguin et al. | |
| 7,914,569 B2 | 3/2011 | Nguyen et al. | |
| 7,959,666 B2 | 6/2011 | Salahieh et al. | |
| 7,959,672 B2 | 6/2011 | Salahieh et al. | |
| 7,972,378 B2 | 7/2011 | Tabor et al. | |
| 7,988,724 B2 | 8/2011 | Salahieh et al. | |
| 7,993,394 B2 | 8/2011 | Hariton et al. | |
| 8,016,877 B2 | 9/2011 | Seguin et al. | |
| D648,854 S | 11/2011 | Braido | |
| 8,048,153 B2 | 11/2011 | Salahieh et al. | |
| 8,052,741 B2 | 11/2011 | Bruszewski et al. | |
| 8,052,749 B2 | 11/2011 | Salahieh et al. | |
| 8,052,750 B2 | 11/2011 | Tuval et al. | |
| 8,062,355 B2 | 11/2011 | Figulla et al. | |
| 8,075,611 B2 | 12/2011 | Millwee et al. | |
| D652,926 S | 1/2012 | Braido | |
| D652,927 S | 1/2012 | Braido et al. | |
| D653,341 S | 1/2012 | Braido et al. | |
| D653,342 S | 1/2012 | Braido et al. | |
| D653,343 S | 1/2012 | Ness et al. | |
| D654,169 S | 2/2012 | Braido | |
| D654,170 S | 2/2012 | Braido et al. | |
| 8,137,398 B2 | 3/2012 | Tuval et al. | |
| 8,142,497 B2 | 3/2012 | Friedman | |
| D660,432 S | 5/2012 | Braido | |
| D660,433 S | 5/2012 | Braido et al. | |
| D660,967 S | 5/2012 | Braido et al. | |
| 8,182,528 B2 | 5/2012 | Salahieh et al. | |
| 8,221,493 B2 | 7/2012 | Boyle et al. | |
| 8,230,717 B2 | 7/2012 | Matonick | |
| 8,231,670 B2 | 7/2012 | Salahieh et al. | |
| 8,252,051 B2 | 8/2012 | Chau et al. | |
| 8,308,798 B2 | 11/2012 | Pintor et al. | |
| 8,313,525 B2 | 11/2012 | Tuval et al. | |
| 8,323,335 B2 | 12/2012 | Rowe et al. | |
| 8,323,336 B2 | 12/2012 | Hill et al. | |
| 8,343,213 B2 | 1/2013 | Salahieh et al. | |
| 8,348,995 B2 | 1/2013 | Tuval et al. | |
| 8,348,996 B2 | 1/2013 | Tuval et al. | |
| 8,348,998 B2 | 1/2013 | Pintor et al. | |
| 8,366,769 B2 | 2/2013 | Huynh et al. | |
| 8,403,983 B2 | 3/2013 | Quadri et al. | |
| 8,408,214 B2 | 4/2013 | Spenser | |
| 8,414,643 B2 | 4/2013 | Tuval et al. | |
| 8,425,593 B2 | 4/2013 | Braido et al. | |
| 8,449,599 B2 | 5/2013 | Chau et al. | |
| 8,449,604 B2 | 5/2013 | Moaddeb et al. | |
| D684,692 S | 6/2013 | Braido | |
| 8,454,686 B2 | 6/2013 | Alkhatib | |
| 8,500,798 B2 | 8/2013 | Rowe et al. | |
| 8,568,474 B2 | 10/2013 | Yeung et al. | |
| 8,579,962 B2 | 11/2013 | Salahieh et al. | |
| 8,579,966 B2 | 11/2013 | Seguin et al. | |
| 8,585,755 B2 | 11/2013 | Chau et al. | |
| 8,591,575 B2 | 11/2013 | Cribier | |
| 8,597,349 B2 | 12/2013 | Alkhatib | |
| 8,603,159 B2 | 12/2013 | Seguin et al. | |
| 8,603,160 B2 | 12/2013 | Salahieh et al. | |
| 8,613,765 B2 | 12/2013 | Bonhoeffer et al. | |
| 8,623,074 B2 | 1/2014 | Ryan | |
| 8,652,204 B2 | 2/2014 | Quill et al. | |
| 8,663,322 B2 | 3/2014 | Keranen | |
| 8,668,733 B2 | 3/2014 | Haug et al. | |
| 8,685,080 B2 | 4/2014 | White | |
| 8,728,154 B2 | 5/2014 | Alkhatib | |
| 8,747,459 B2 | 6/2014 | Nguyen et al. | |
| 8,764,820 B2 | 7/2014 | Dehdashtian et al. | |
| 8,795,357 B2 | 8/2014 | Yohanan et al. | |
| 8,801,776 B2 | 8/2014 | House et al. | |
| 8,808,356 B2 | 8/2014 | Braido et al. | |
| 8,828,078 B2 | 9/2014 | Salahieh et al. | |
| 8,834,563 B2 | 9/2014 | Righini | |
| 8,840,661 B2 | 9/2014 | Manasse | |
| 8,840,663 B2 | 9/2014 | Salahieh et al. | |

(56) References Cited

U.S. PATENT DOCUMENTS

| | | |
|---|---|---|
| 8,876,894 B2 | 11/2014 | Tuval et al. |
| 8,876,895 B2 | 11/2014 | Tuval et al. |
| 8,940,040 B2 | 1/2015 | Shahriari |
| 8,945,209 B2 | 2/2015 | Bonyuet et al. |
| 8,961,595 B2 | 2/2015 | Alkhatib |
| 8,974,523 B2 | 3/2015 | Thill et al. |
| 8,974,524 B2 | 3/2015 | Yeung et al. |
| 9,326,856 B2 | 5/2016 | Schraut et al. |
| 9,889,004 B2* | 2/2018 | Braido ............... A61F 2/2418 |
| 2002/0036220 A1 | 3/2002 | Gabbay |
| 2003/0014104 A1* | 1/2003 | Cribier ............... A61F 2/2412 623/2.11 |
| 2003/0023303 A1 | 1/2003 | Palmaz et al. |
| 2003/0050694 A1 | 3/2003 | Yang et al. |
| 2003/0130726 A1 | 7/2003 | Thorpe et al. |
| 2004/0049262 A1 | 3/2004 | Obermiller et al. |
| 2004/0093075 A1 | 5/2004 | Kuehne |
| 2004/0111111 A1 | 6/2004 | Lin |
| 2004/0186563 A1 | 9/2004 | Lobbi |
| 2004/0210304 A1 | 10/2004 | Seguin et al. |
| 2004/0260389 A1 | 12/2004 | Case et al. |
| 2005/0075720 A1 | 4/2005 | Nguyen et al. |
| 2005/0096726 A1 | 5/2005 | Sequin et al. |
| 2005/0137682 A1 | 6/2005 | Justino |
| 2005/0137687 A1 | 6/2005 | Salahieh et al. |
| 2005/0137695 A1 | 6/2005 | Salahieh et al. |
| 2005/0137697 A1 | 6/2005 | Salahieh et al. |
| 2005/0137701 A1 | 6/2005 | Salahieh et al. |
| 2005/0203605 A1 | 9/2005 | Dolan |
| 2005/0240200 A1 | 10/2005 | Bergheim |
| 2005/0256566 A1 | 11/2005 | Gabbay |
| 2006/0008497 A1 | 1/2006 | Gabbay |
| 2006/0074484 A1 | 4/2006 | Huber |
| 2006/0106415 A1 | 5/2006 | Gabbay |
| 2006/0122692 A1 | 6/2006 | Gilad et al. |
| 2006/0142848 A1 | 6/2006 | Gabbay |
| 2006/0149360 A1 | 7/2006 | Schwammenthal et al. |
| 2006/0161249 A1 | 7/2006 | Realyvasquez et al. |
| 2006/0167468 A1 | 7/2006 | Gabbay |
| 2006/0173532 A1 | 8/2006 | Flagle et al. |
| 2006/0178740 A1 | 8/2006 | Stacchino et al. |
| 2006/0195180 A1 | 8/2006 | Kheradvar et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2006/0276874 A1 | 12/2006 | Wilson et al. |
| 2006/0287717 A1 | 12/2006 | Rowe et al. |
| 2007/0010876 A1 | 1/2007 | Salahieh et al. |
| 2007/0027534 A1 | 2/2007 | Bergheim et al. |
| 2007/0043431 A1 | 2/2007 | Melsheimer |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0073387 A1 | 3/2007 | Forster et al. |
| 2007/0073391 A1 | 3/2007 | Bourang et al. |
| 2007/0088431 A1 | 4/2007 | Bourang et al. |
| 2007/0093890 A1 | 4/2007 | Eliasen et al. |
| 2007/0100435 A1 | 5/2007 | Case et al. |
| 2007/0112422 A1 | 5/2007 | Dehdashtian |
| 2007/0118210 A1 | 5/2007 | Pinchuk |
| 2007/0162100 A1 | 7/2007 | Gabbay |
| 2007/0168013 A1 | 7/2007 | Douglas |
| 2007/0203575 A1 | 8/2007 | Forster et al. |
| 2007/0213813 A1 | 9/2007 | Von Segesser et al. |
| 2007/0233228 A1 | 10/2007 | Eberhardt et al. |
| 2007/0239271 A1 | 10/2007 | Nguyen |
| 2007/0244545 A1 | 10/2007 | Birdsall et al. |
| 2007/0244552 A1 | 10/2007 | Salahieh et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147182 A1 | 6/2008 | Righini et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0054975 A1 | 2/2009 | del Nido et al. |
| 2009/0099653 A1 | 4/2009 | Suri et al. |
| 2009/0112309 A1 | 4/2009 | Jaramillo et al. |
| 2009/0138079 A1 | 5/2009 | Tuval et al. |
| 2009/0276027 A1 | 11/2009 | Glynn |
| 2009/0276040 A1 | 11/2009 | Rowe et al. |
| 2009/0287299 A1 | 11/2009 | Tabor et al. |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0082094 A1 | 4/2010 | Quadri et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0168844 A1 | 7/2010 | Toomes et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0234940 A1 | 9/2010 | Dolan |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0054466 A1 | 3/2011 | Rothstein et al. |
| 2011/0098800 A1 | 4/2011 | Braido et al. |
| 2011/0098802 A1 | 4/2011 | Braido et al. |
| 2011/0137397 A1 | 6/2011 | Chau et al. |
| 2011/0172765 A1 | 7/2011 | Nguyen et al. |
| 2011/0208283 A1 | 8/2011 | Rust |
| 2011/0224678 A1 | 9/2011 | Gabbay |
| 2011/0238168 A1 | 9/2011 | Pellegrini et al. |
| 2011/0264206 A1 | 10/2011 | Tabor |
| 2011/0295363 A1 | 12/2011 | Girard et al. |
| 2012/0035722 A1 | 2/2012 | Tuval |
| 2012/0041550 A1 | 2/2012 | Salahieh et al. |
| 2012/0053681 A1 | 3/2012 | Alkhatib et al. |
| 2012/0071969 A1 | 3/2012 | Li et al. |
| 2012/0078347 A1 | 3/2012 | Braido et al. |
| 2012/0078350 A1 | 3/2012 | Wang et al. |
| 2012/0101572 A1 | 4/2012 | Kovalsky et al. |
| 2012/0123529 A1 | 5/2012 | Levi et al. |
| 2012/0143324 A1 | 6/2012 | Rankin et al. |
| 2012/0303116 A1 | 11/2012 | Gorman, III et al. |
| 2013/0018458 A1 | 1/2013 | Yohanan et al. |
| 2013/0274873 A1* | 10/2013 | Delaloye ............... A61F 2/2409 623/2.18 |
| 2013/0304200 A1 | 11/2013 | McLean et al. |
| 2013/0331929 A1 | 12/2013 | Mitra et al. |
| 2014/0005771 A1 | 1/2014 | Braido et al. |
| 2014/0121763 A1 | 5/2014 | Duffy et al. |
| 2014/0155997 A1 | 6/2014 | Braido |
| 2014/0214159 A1 | 7/2014 | Vidlund et al. |
| 2014/0228946 A1 | 8/2014 | Chau et al. |
| 2014/0277419 A1* | 9/2014 | Garde ............... A61F 2/2403 623/2.18 |
| 2014/0277423 A1* | 9/2014 | Alkhatib ............... A61F 2/2418 623/2.38 |
| 2014/0303719 A1 | 10/2014 | Cox et al. |
| 2014/0324164 A1 | 10/2014 | Gross et al. |

(56) References Cited

U.S. PATENT DOCUMENTS

| | | | |
|---|---|---|---|
| 2014/0343671 A1 | 11/2014 | Yohanan et al. | |
| 2014/0350668 A1 | 11/2014 | Delaloye et al. | |
| 2014/0350669 A1 | 11/2014 | Gillespie et al. | |

FOREIGN PATENT DOCUMENTS

| | | |
|---|---|---|
| DE | 102005003632 A1 | 8/2006 |
| DE | 202008009610 U1 | 12/2008 |
| EP | 0850607 A1 | 7/1998 |
| EP | 1000590 A1 | 5/2000 |
| EP | 1129744 A1 | 9/2001 |
| EP | 1157673 A2 | 11/2001 |
| EP | 1360942 A1 | 11/2003 |
| EP | 1584306 A1 | 10/2005 |
| EP | 1598031 A2 | 11/2005 |
| EP | 1926455 A2 | 6/2008 |
| EP | 2537487 A1 | 12/2012 |
| EP | 2870946 A1 | 5/2015 |
| FR | 2850008 A1 | 7/2004 |
| FR | 2847800 B1 | 10/2005 |
| WO | 9117720 A1 | 11/1991 |
| WO | 9716133 A1 | 5/1997 |
| WO | 9832412 A2 | 7/1998 |
| WO | 991801 A1 | 3/1999 |
| WO | 0128459 A1 | 4/2001 |
| WO | 0149213 A2 | 7/2001 |
| WO | 0154625 A1 | 8/2001 |
| WO | 0156500 A2 | 8/2001 |
| WO | 0176510 A2 | 10/2001 |
| WO | 2001076510 A2 | 10/2001 |
| WO | 0236048 A1 | 5/2002 |
| WO | 0247575 A2 | 6/2002 |
| WO | 02067782 A2 | 9/2002 |
| WO | 03047468 A1 | 6/2003 |
| WO | 2005070343 A1 | 8/2005 |
| WO | 06073626 A2 | 7/2006 |
| WO | 2007053243 A2 | 5/2007 |
| WO | 07071436 A2 | 6/2007 |
| WO | 08070797 A2 | 6/2008 |
| WO | 2009042196 A2 | 4/2009 |
| WO | 2010008548 A2 | 1/2010 |
| WO | 2010008549 A1 | 1/2010 |
| WO | 10051025 A1 | 5/2010 |
| WO | 10087975 A1 | 8/2010 |
| WO | 2010096176 A1 | 8/2010 |
| WO | 2010098857 A1 | 9/2010 |
| WO | 2013/028387 A2 | 2/2013 |
| WO | 2014163704 A1 | 10/2014 |
| WO | 2014164149 | 10/2014 |
| WO | 2014164151 A1 | 10/2014 |
| WO | 2015077274 A1 | 5/2015 |

OTHER PUBLICATIONS

Knudsen, L.L. et al., "Catheter-implanted prosthetic heart valves," The International Journal of Artificial Organs, May 1993, pp. 253-262, vol. 16, No. 5.
Moazami, N. et al., Transluminal Aortic Valve Placement, ASAIO Journal, Sep.-Oct. 1996; pp. M381-M385, vol. 42, No. 5.
Andersen, H.R., "Transluminal Catheter Implanted Prosthetic Heart Valves," International Journal of Angiology, Mar. 1998, pp. 102-106, vol. 7, No. 2.
Andersen, H.R. et al, "Transluminal implantation of artificial heart valves," European Heart Journal, May 1992, pp. 704-708, vol. 13, No. 5.
Zegdi, R., MD, PhD et al., "Is It Reasonable to Treat All Calcified Stenotic Aortic Valves With a Valved Stent?" J. of the American College of Cardiology, Feb. 5, 2008, pp. 579-584, vol. 51, No. 5.
Ruiz, C., "Overview of PRE-CE Mark Transcatheter Aortic Valve Technologies," Euro PCR, May 2010 (Powerpoint dated May 25, 2010).
Quaden, R. et al., "Percutaneous aortic valve replacement: resection before implantation," European J. of Cardio-thoracic Surgery, May 2005, pp. 836-840, vol. 27, No. 5.
U.S. Appl. No. 29/375,243, filed Sep. 20, 2010.
U.S. Appl. No. 29/375,260, filed Sep. 20, 2010.
International Search Report for Application No. PCT/US2015/011387 dated Mar. 30, 2015.
International Search Report for Application No. PCT/US2014/054485 dated Nov. 20, 2014.
Extended European Search Report for Application No. 15152315.6 dated May 29, 2015.
Extended European Search Report for Application No. 15152324.8 dated Jun. 10, 2015.
Rohde, et al., "Resection of Calcified Aortic Heart Leaflets In Vitro by Q-Switched 2 µm Microsecond Laser Radiation", Journal of Cardiac Surgery, 30(2):157-62. Feb. 2015.
Muñoz, et al., "Guidance of treatment of perivalvular prosthetic leaks.", Current cardiology reports, 16.430, 6 pages, Jan. 2014.
Gössl, Mario, and Charanjit S. Rihal. "Percutaneous treatment of aortic and mitral valve paravalvular regurgitation." Current cardiology reports 15.8 (2013): 1-8.
Swiatkiewicz, Iwona, et al. "Percutaneous closure of mitral perivalvular leak." Kardiologia polska 67.7 (2009): 762.
De Cicco, Giuseppe, et al. "Aortic valve periprosthetic leakage: anatomic observations and surgical results." The Annals of thoracic surgery 79.5 (2005): 1480-1485.
Heat Advisor, "Heart repairs without surgery. Minimally invasive procedures aim to correct valve leakage", Sep. 2004, PubMed ID 15586429.
Transcatheter Umbrella Closure of Valvular and Paravalvular Leaks, Hourihan et al., Journal of the American College of Cardiology, vol. 20, No. 6, pp. 1371-1377, (1992).
Buellesfeld et al., Treatment of paravalvular leaks through interventional techniques; Department of Cardiology, Ben University Hospital 2011.
"Direct-Access Valve Replacement", Christoph H. Huber, et al., Journal of the American College of Cardiology, vol. 46, No. 2, (Jul. 19, 2005).
"Percutaneous Aortic Valve Implantation Retrograde From the Femoral Artery", John G. Webb et al., Circulation, 2006; 113:842-850 (Feb. 6, 2006).
"Minimally invasive cardiac surgery", M. J. Mack, Surgical Endoscopy, 2006, 20:S488-S492, DOI: 10.1007/s00464-006-0110-8 (presented Apr. 24, 2006).
"Transapical Transcatheter Aortic Valve Implantation in Humans", Samuel V. Lichtenstein et al., Circulation. 2006; 114: 591-596 (Jul. 31, 2006).
"Closed heart surgery: Back to the future", Samuel V. Lichtenstein, The Journal of Thoracic and Cardiovascular Surgery, vol. 131, No. 5, pp. 941-943.
"Transapical approach for sutureless stent-fixed aortic valve implantation: experimental results"; Th. Walther et al., European Journal of Cardio-thoracic Surgery 29 (2006) 703-708 (Jan. 30, 2006).
"Transapical aortic valve implantation: an animal feasibility study"; Todd M. Dewey et al., The annals of thoracic surgery 2006; 82: 110-6 (Feb. 13, 2006).
Textbook "Transcatheter Valve Repair", 2006, pp. 165-186.

* cited by examiner

SEALING STRUCTURES FOR PARAVALVULAR LEAK PROTECTION

CROSS-REFERENCE TO RELATED APPLICATIONS

This application is a divisional of U.S. application Ser. No. 14/547,595, filed on Nov. 19, 2014, which claims the benefit of the filing date of U.S. Provisional Patent Application No. 61/906,076, filed on Nov. 19, 2013, the disclosures of which are hereby incorporated herein by reference.

BACKGROUND OF THE INVENTION

The present disclosure relates in general to heart valve replacement and, in particular, to collapsible prosthetic heart valves. More particularly, the present disclosure relates to devices and methods for positioning and sealing collapsible prosthetic heart valves within a native valve annulus.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two common types of stents on which the valve structures are ordinarily mounted: a self-expanding stent or a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, and then expanding a balloon positioned within the valve stent. For self-expanding valves, on the other hand, the stent automatically expands as the sheath covering the valve is withdrawn.

SUMMARY OF THE INVENTION

In some embodiments, a prosthetic heart valve for replacing a native valve includes a collapsible and expandable stent having a proximal end and a distal end and a valve assembly disposed within the stent, the valve assembly including a plurality of leaflets. The heart valve further includes a cuff annularly disposed about the stent and having a surplus portion capable of forming a sealing structure at the proximal end of the stent, the sealing structure having a deployed condition with a diameter in the deployed condition greater than a diameter of the proximal end of the stent.

In some embodiments, a prosthetic heart valve for replacing a native valve includes a collapsible and expandable stent having a proximal end and a distal end, a valve assembly disposed within the stent, the valve assembly including a plurality of leaflets and a cuff annularly disposed about the stent and having an attached end coupled to the stent and a free end extending past the proximal end of the strut and capable of forming a sealing structure for sealing gaps between the prosthetic heart valve and a native valve annulus.

In some embodiments, a method of making a prosthetic heart valve for replacing a native valve includes providing a collapsible and expandable stent having a proximal end and a distal end, coupling a valve assembly to the stent, the valve assembly including a plurality of leaflets, coupling a cuff to the stent so that a surplus portion of the cuff extends beyond the proximal end of the strut and converting the surplus portion of the cuff into a sealing structure at the proximal end of the stent, the sealing structure having a diameter greater than a diameter of the proximal end of the stent.

BRIEF DESCRIPTION OF THE DRAWINGS

Various embodiments of the present invention will now be described with reference to the appended drawings. It is to be appreciated that these drawings depict only some embodiments of the invention and are therefore not to be considered limiting of its scope.

DETAILED DESCRIPTION

Figure 1:
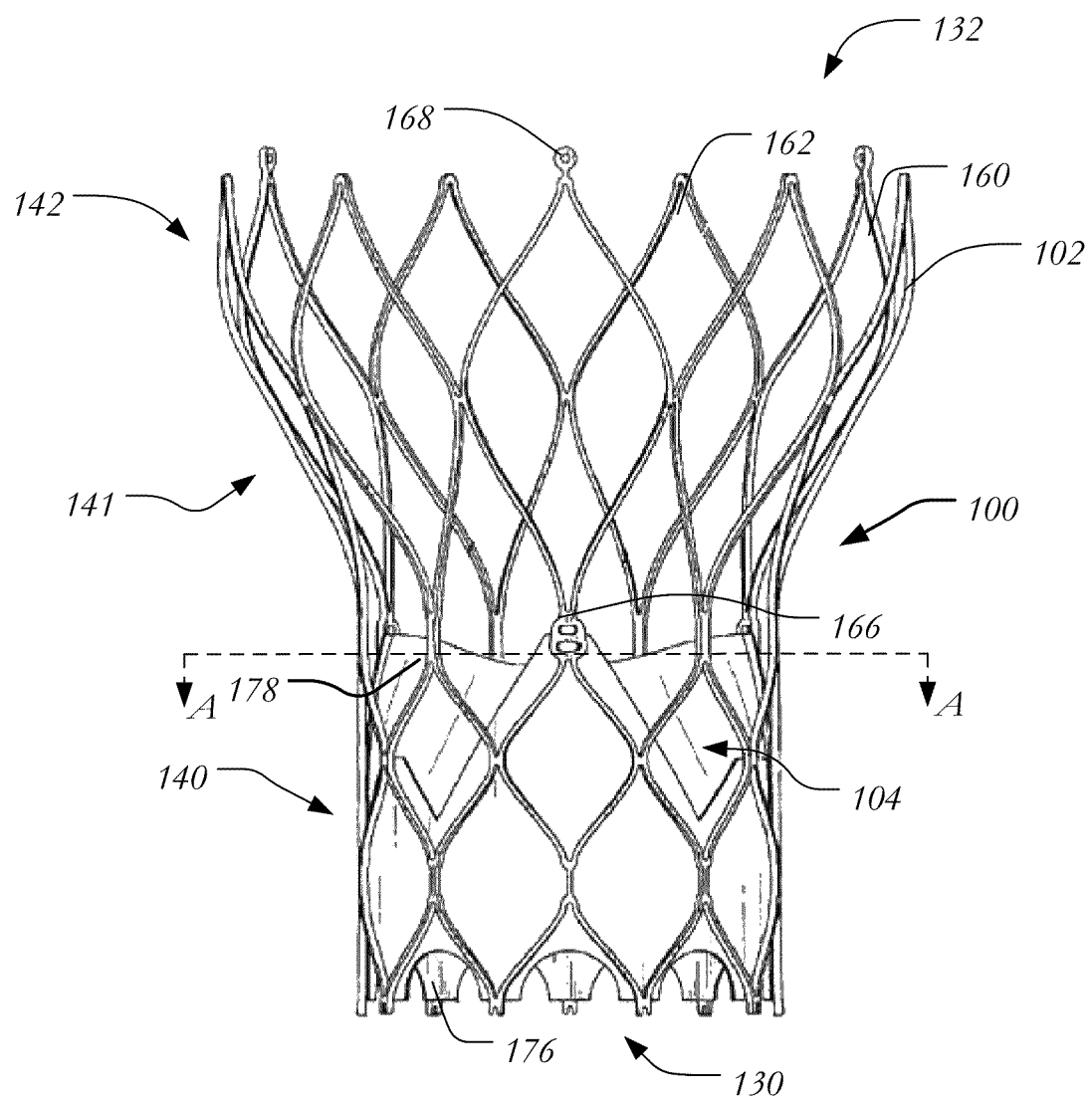
FIG. 1 is a side elevational view of a conventional prosthetic heart valve.

Despite the various improvements that have been made to the collapsible prosthetic heart valve delivery process, conventional devices suffer from some shortcomings. For example, with conventional self expanding valves, clinical success of the valve is dependent on accurate deployment and anchoring. Inaccurate deployment and anchoring of the valve increases risks, such as those associated with valve migration, which may cause severe complications and possibly death due to the obstruction of the left ventricular outflow tract. Inaccurate deployment and anchoring may also result in the leakage of blood between the implanted heart valve and the native valve annulus, commonly referred to as perivalvular leakage (also known as "paravalvular leakage"). In aortic valves, this leakage enables blood to flow from the aorta back into the left ventricle, reducing cardiac efficiency and putting a greater strain on the heart muscle. Additionally, calcification of the aortic valve may affect performance and the interaction between the implanted valve and the calcified tissue is believed to be relevant to leakage, as will be outlined below.

Moreover, anatomical variations from one patient to another may cause a fully deployed heart valve to function improperly, requiring removal of the valve from the patient. Removing a fully deployed heart valve increases the length of the procedure as well as the risk of infection and/or damage to heart tissue. Thus, methods and devices are desirable that would reduce the need to remove a prosthetic heart valve from a patient. Methods and devices are also desirable that would reduce the likelihood of perivalvular leakage due to gaps between the implanted heart valve and patient tissue.

There therefore is a need for further improvements to the devices, systems, and methods for transcatheter delivery and positioning of collapsible prosthetic heart valves. Specifically, there is a need for further improvements to the devices, systems, and methods for accurately implanting a prosthetic heart valve. Among other advantages, the present disclosure may address one or more of these needs.

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient. When used in connection with devices for delivering a prosthetic heart valve or other medical device into a patient, the terms "trailing" and "leading" are to be taken as relative to the user of the delivery devices. "Trailing" is to be understood as relatively close to the user, and "leading" is to be understood as relatively farther away from the user. Also as used herein, the terms "generally," "substantially," and "about" are intended to mean that slight deviations from absolute are included within the scope of the term so modified.

The sealing portions of the present disclosure may be used in connection with collapsible prosthetic heart valves. FIG. 1 shows one such collapsible stent-supported prosthetic heart valve 100 including a stent 102 and a valve assembly 104 as is known in the art. The prosthetic heart valve 100 is designed to replace a native tricuspid valve of a patient, such as a native aortic valve. It should be noted that while the inventions herein are described predominantly in connection with their use with a prosthetic aortic valve and a stent having a shape as illustrated in FIG. 1, the valve could be a bicuspid valve, such as the mitral valve, and the stent could have different shapes, such as a flared or conical annulus section, a less-bulbous aortic section, and the like, and a differently shaped transition section.

Prosthetic heart valve 100 will be described in more detail with reference to FIG. 1. Prosthetic heart valve 100 includes expandable stent 102 which may be formed from biocompatible materials that are capable of self-expansion, such as, for example, shape memory alloys, such as the nickel-titanium alloy known as "Nitinol" or other suitable metals or polymers. Stent 102 extends from a proximal or annulus end 130 to a distal or aortic end 132, and includes annulus section 140 adjacent proximal end 130, transition section 141 and aortic section 142 adjacent distal end 132. Annulus section 140 has a relatively small cross-section in the expanded condition, while aortic section 142 has a relatively large cross-section in the expanded condition. Preferably, annulus section 140 is in the form of a cylinder having a substantially constant diameter along its length. Transition section 141 may taper outwardly from annulus section 140 to aortic section 142. Each of the sections of stent 102 includes a plurality of struts 160 forming cells 162 connected to one another in one or more annular rows around the stent. For example, as shown in FIG. 1, annulus section 140 may have two annular rows of complete cells 162 and aortic section 142 and transition section 141 may each have one or more annular rows of partial cells 162. Cells 162 in aortic section 142 may be larger than cells 162 in annulus section 140. The larger cells in aortic section 142 better enable prosthetic valve 100 to be positioned in the native valve annulus without the stent structure interfering with blood flow to the coronary arteries.

Stent 102 may include one or more retaining elements 168 at distal end 132 thereof, retaining elements 168 being sized and shaped to cooperate with female retaining structures (not shown) provided on the deployment device. The engagement of retaining elements 168 with the female retaining structures on the deployment device helps maintain prosthetic heart valve 100 in assembled relationship with the deployment device, minimizes longitudinal movement of the prosthetic heart valve relative to the deployment device during unsheathing or resheathing procedures, and helps prevent rotation of the prosthetic heart valve relative to the deployment device as the deployment device is advanced to the target location and the heart valve deployed.

Prosthetic heart valve 100 includes valve assembly 104 preferably positioned in annulus section 140 of the stent 102 and secured to the stent. Valve assembly 104 includes cuff 176 and a plurality of leaflets 178 which collectively function as a one-way valve by coapting with one another. As a prosthetic aortic valve, valve 100 has three leaflets 178. However, it will be appreciated that other prosthetic heart valves with which the sealing portions of the present disclosure may be used may have a greater or lesser number of leaflets 178.

Although cuff 176 is shown in FIG. 1 as being disposed on the luminal or inner surface of annulus section 140, it is contemplated that cuff 176 may be disposed on the abluminal or outer surface of annulus section 140 or may cover all or part of either or both of the luminal and abluminal surfaces. Both cuff 176 and leaflets 178 may be wholly or partly formed of any suitable biological material or polymer such as, for example, polytetrafluoroethylene (PTFE), polyvinyl alcohol (PVA), ultra-high molecular weight polyethylene, silicone, urethane and the like.

Leaflets 178 may be attached along their belly portions to cells 162 of stent 102, with the commissure between adjacent leaflets 178 attached to commissure features 166. As can be seen in FIG. 1, each commissure feature 166 may lie at the intersection of four cells 162, two of the cells being adjacent one another in the same annular row, and the other two cells being in different annular rows and lying in end-to-end relationship. Preferably, commissure features 166 are positioned entirely within annulus section 140 or at the juncture of annulus section 140 and transition section 141. Commissure features 166 may include one or more eyelets which facilitate the suturing of the leaflet commissure to stent 102.

Prosthetic heart valve 100 may be used to replace a native aortic valve, a surgical heart valve or a heart valve that has undergone a surgical procedure. Prosthetic heart valve 100 may be delivered to the desired site (e.g., near the native aortic annulus) using any suitable delivery device. During delivery, prosthetic heart valve 100 is disposed inside the delivery device in the collapsed condition. The delivery device may be introduced into a patient using a transfemoral, transapical, transseptal, transradial, transsubclavian, transaortic or any other percutaneous approach. Once the delivery device has reached the target site, the user may deploy prosthetic heart valve 100. Upon deployment, prosthetic heart valve 100 expands so that annulus section 140 is in secure engagement within the native aortic annulus. When prosthetic heart valve 100 is properly positioned inside the heart, it works as a one-way valve, allowing blood to flow from the left ventricle of the heart to the aorta, and preventing blood from flowing in the opposite direction.

Problems may be encountered when implanting prosthetic heart valve 100. For example, in certain procedures, collapsible valves may be implanted in a native valve annulus without first resecting the native valve leaflets. The collapsible valves may have critical clinical issues because of the nature of the stenotic leaflets that are left in place. Additionally, patients with uneven calcification, bi-cuspid aortic valve disease, and/or valve insufficiency cannot be treated well, if at all, with the current collapsible valve designs.

The reliance on unevenly calcified leaflets for proper valve placement and seating could lead to several problems, such as perivalvular leakage (PV leak), which can have severe adverse clinical outcomes. To reduce these adverse events, the optimal valve would anchor adequately and seal without the need for excessive radial force that could harm nearby anatomy and physiology.

Figure 2A:
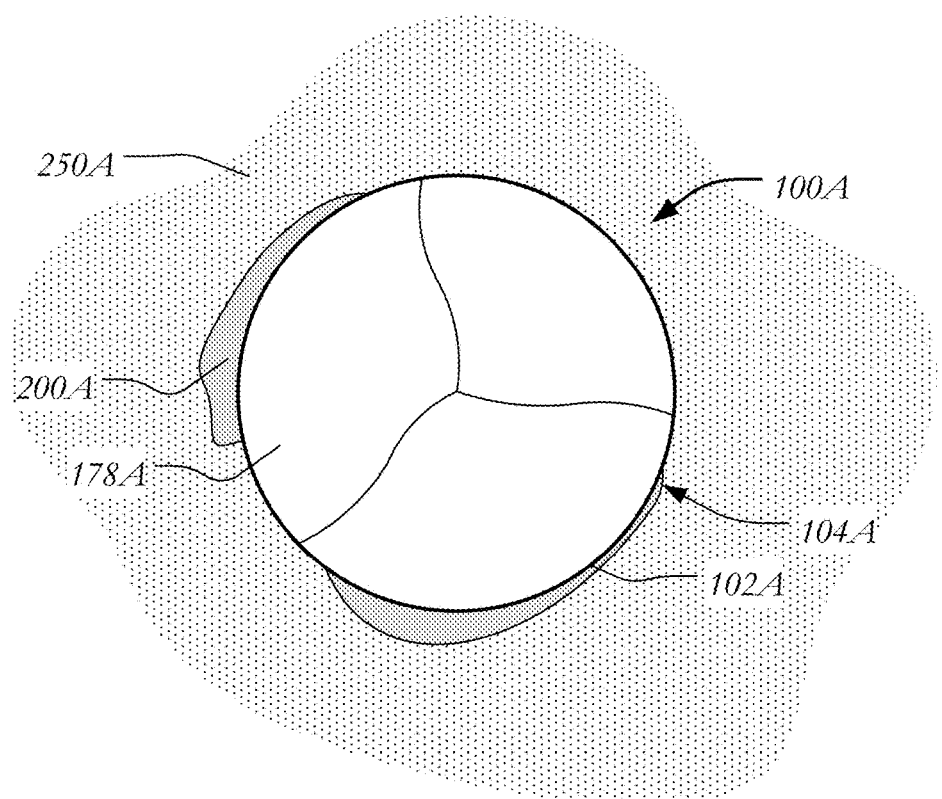
FIG. 2A is a highly schematic cross-sectional view taken along line A-A of FIG. 1 and showing the prosthetic heart valve disposed within a native valve annulus.

FIG. 2A is a highly schematic cross-sectional illustration of a prosthetic aortic valve 100A disposed within native valve annulus 250A. As seen in the figure, valve assembly 104A has a substantially circular cross-section which is disposed within the non-circular native valve annulus 250A. At certain locations around the perimeter of heart valve 100A, gaps 200A form between heart valve 100A and native valve annulus 250A. Blood flowing through these gaps and past valve assembly 104A of prosthetic heart valve 100A can cause regurgitation and other inefficiencies which reduce cardiac performance. Such improper fitment may be due to suboptimal native valve annulus geometry due, for example, to calcification of native valve annulus 250A or to unresected native leaflets.

Figure 2B:
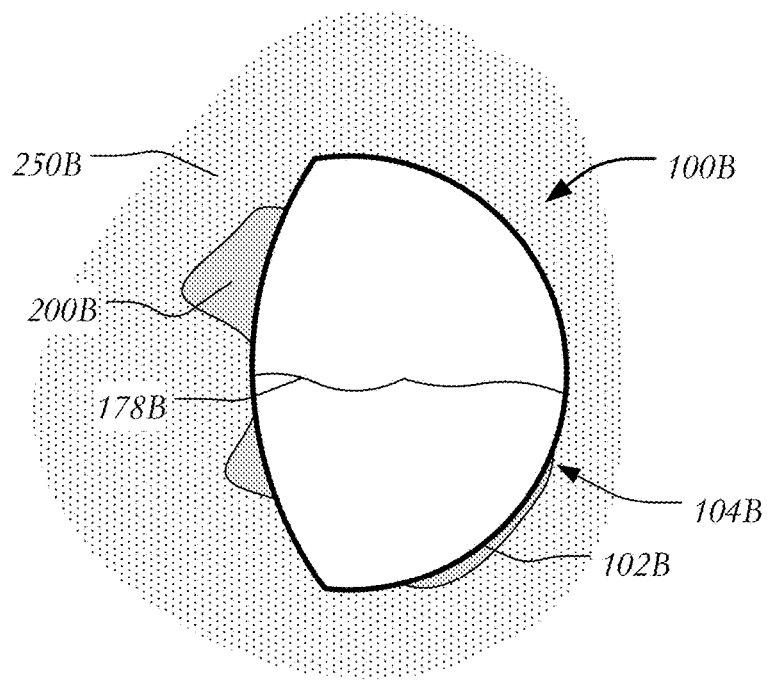
FIG. 2B is a highly schematic cross-sectional view showing a prosthetic mitral valve disposed within a native valve annulus.

FIG. 2B is a similar cross-sectional illustration of a prosthetic mitral valve 100B disposed within native valve annulus 250B. As seen in the figure, valve assembly 104B has a substantially D-shaped cross-section which is disposed within irregularly-shaped annulus 250B. At certain locations around the perimeter of heart valve 100B, gaps 200B form between heart valve 100B and native valve annulus 250B. Regurgitation and other inefficiencies may thus result in a prosthetic mitral valve. Though the following examples show aortic valves, it will be understood that the present devices and methods may be equally applicable to mitral heart valves.

Figure 3A:
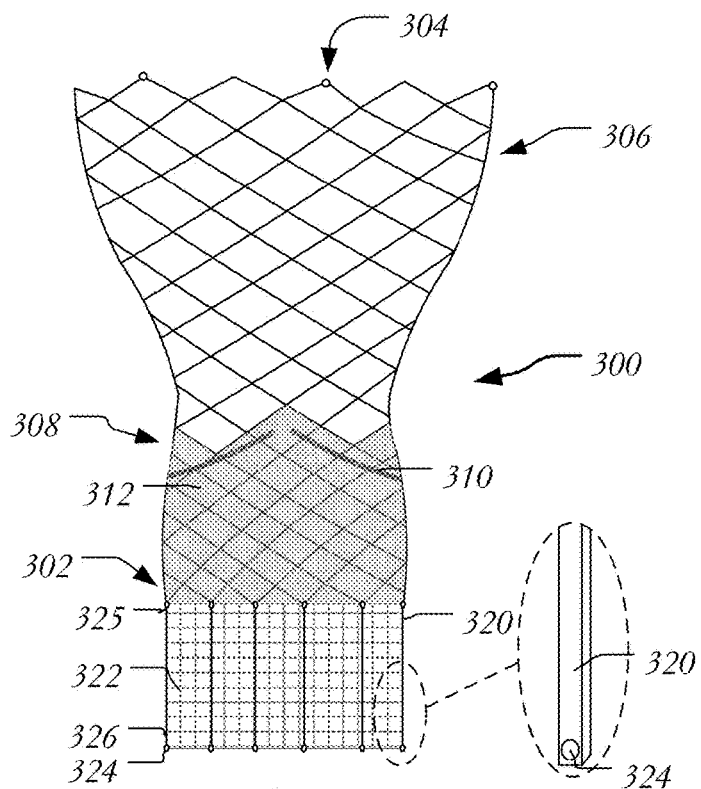
FIGS. 3A and 3B are highly schematic side views of one embodiment of a heart valve having a sealing portion intended to fill irregularities between the heart valve and the native valve annulus.
Figure 3B:
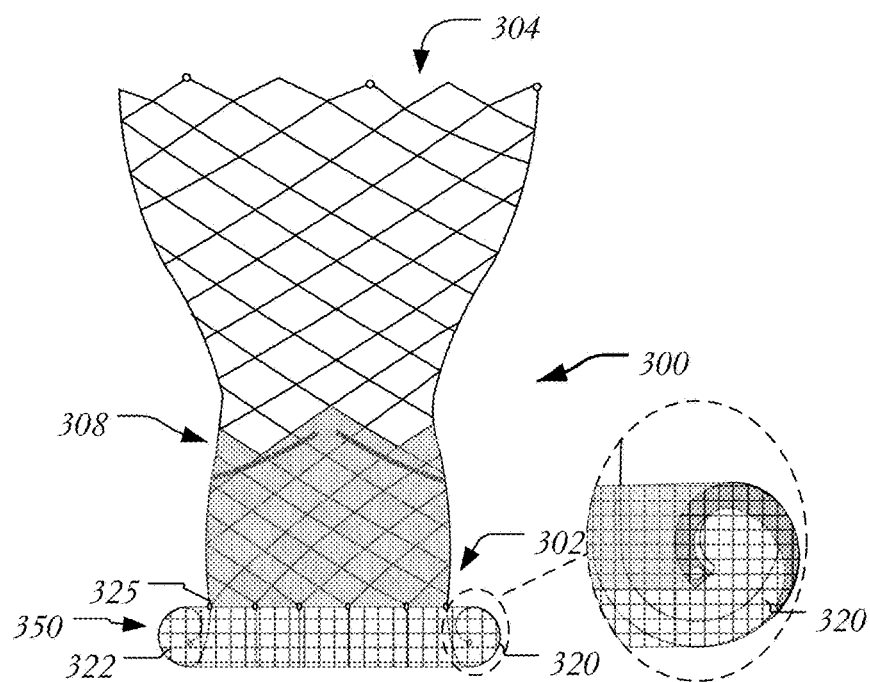

FIGS. 3A and 3B illustrate one embodiment of heart valve 300 intended to fill the irregularities between the heart valve and native valve annulus 250A shown in FIG. 2A. Heart valve 300 extends between proximal end 302 and distal end 304, and may generally include stent 306 and valve assembly 308 having a plurality of leaflets 310 and cuff 312. Heart valve 300 may be formed of any of the materials and in any of the configurations described above with reference to FIG. 1.

Additionally, heart valve 300 may include a number of elongated legs 320 and a sealing portion 322 coupled to the elongated legs via eyelets 324 to mitigate perivalvular leakage. Attachment ends 325 of elongated legs 320 may be affixed to stent 306 near the proximal end 302 of heart valve 300, and legs 320 may extend away from the distal end 304 of stent 306 and terminate at free ends 326, which are unattached and free to move. As will be shown in subsequent examples, elongated legs 320 may instead be oriented in the opposition direction, being affixed near the proximal end 302 of heart valve 300 and extending toward the distal end 304 of the heart valve. Attachment ends 325 of elongated legs 320 may be affixed to stent 306 using welding, adhesive, or any other suitable technique known in the art. Additionally, legs 320 may be formed of a shape memory material such as those described above for forming stent 102 of FIG. 1, and may have an extended configuration and a relaxed configuration. In the extended configuration, shown in FIG. 3A, elongated legs 320 may be substantially linear. Moreover, instead of being separately formed and affixed to stent 306 at attachment ends 325, elongated legs 320 may be integrally formed with stent 306, such as by laser cutting both stent 306 and elongated legs 320 from the same tube.

Sealing portion 322 may be attached to legs 320 to form a cylindrical tube around the interior or exterior of the legs. Sealing portion 322 may be attached to legs 320 via sutures, adhesive or any other suitable method. For example, each leg 320 may include eyelets 324 and sealing portion 322 may be attached to eyelets 324 via sutures (not shown). Where eyelets 324 are provided in this or any of the other embodiments described herein, they may be disposed at the free ends of legs 320 as illustrated in FIG. 3A, or anywhere else along the length of the legs. Providing eyelets 324 along the length of legs 320 may better hold sealing portion 322 to the legs as the legs move between their extended and relaxed configurations. Moreover, it will be understood that other features such as indentations or notches may be used to couple two portions of the prosthetic valve using sutures.

Sealing portion 322 may be formed of the same material as cuff 312, including natural materials such as, for example, bovine or porcine pericardium, or synthetic materials such as, for example, ultra-high-molecular-weight polyethylene (UHMWPE), or combinations thereof. In one example, sealing portion 322 may be formed by increasing the length of cuff 312 and extending it over the proximal end 302 and legs 320 of heart valve 300. Alternatively, sealing portion 322 may be formed separately from cuff 312 and attached to eyelets 324 at the proximal end 302 of heart valve 300 to form a seam with cuff 312.

In a variant of the foregoing, sealing portion 322 of heart valve 300 may be formed from a tubular section of braided fabric comprising a plurality of braided strands. The strands forming the braid may have a predetermined relative orientation with respect to one another (e.g., a helical braid). Moreover, sealing portion 322 may comprise a plurality of layers of braided fabric and/or other occluding material such that sealing portion 322 is capable of at least partially inhibiting blood flow therethrough in order to promote the formation of thrombus, endothelialization and epithelialization.

In such variants, sealing portion 322 may be formed of a passive material (e.g., one that does not change shape in response to a stimulus) so that it simply conforms to the shape of legs 320. Alternatively, sealing portion 322 may be formed, for example, of a braided fabric mesh of a shape-memory material, of a super-elastic material, of a biocompatible polymer, or of another material that is capable of being actuated between an extended configuration and a relaxed configuration. Sealing portion 322 may comprise a braided metal fabric that is both resilient and capable of heat treatment to substantially set a desired shape (e.g., the relaxed configuration shown in FIG. 3B). One class of materials which meets these qualifications is shape memory alloys, such as Nitinol. It is also understood that sealing portion 322 may comprise various materials other than Nitinol that have elastic and/or memory properties, such as spring stainless steel, trade named alloys such as Elgiloy®, and Hastelloy®, CoCrNi alloys (e.g., trade name Phynox), MP35N®, CoCrMo alloys, mixtures of such alloys or mixtures of metal and polymer fibers. Depending on the individual material selected, the strand diameter, number of strands, and pitch may be altered to achieve the desired properties for sealing portion 322. Thus, sealing portion 322 may alternate between the extended configuration and the relaxed configuration due to the changing shape of legs 320 or alternatively it may itself alternate between the two configurations due to its own shape-memory material properties.

FIG. 3B illustrates the relaxed configuration of heart valve 300. As noted above, legs 320 may have an extended configuration and a relaxed configuration. To effectuate this change in configuration, legs 320 may be curled and subjected to a heat setting process. This process may be accomplished in a series of steps. For example, legs 320 may be formed with a first curl and heat set, and then formed with a second curl and further heat set. The relaxed configuration of legs 320 may therefore include multiple curls due to the curling and heat setting process described above. Legs 320 may be straightened to the extended configuration (shown in FIG. 3A and described above) for cooperation with a delivery system as will be described below with reference to FIGS. 4A-E, and may return to the curled, relaxed configuration after removal from the delivery system. As shown in FIG. 3B, when heart valve 300 is permitted to return to its relaxed configuration, legs 320 may curl up toward distal end 304 and pull sealing portion 322 with them, rolling sealing portion 322 up in the process to form sealing ring 350 at proximal end 302 of heart valve 300. Sealing ring 350 may have a radius larger than that of valve assembly 308, the larger radius of sealing ring 350 being capable of filling any gaps between heart valve 300 and the native valve annulus (not shown). The length of sealing ring 350 may depend on the number of curls of legs 320. For example, sealing ring 350 may have a length that is approximately one-half of the length of legs 320. As shown in FIG. 3B, sealing ring 350 is formed below proximal end 302 and may be suitable for a sub-leaflet application as will be described in greater detail below with reference to FIGS. 8A-8C. Sealing ring 350 may be readily deformable to conform to the shape of the native valve annulus, portions of sealing ring 350 being configured to compress when pressed against the walls of the native valve annulus and other portions of sealing ring 350 being configured to radially expand in gaps, thereby filling the gaps between heart valve 300 and the native valve annulus.

A method of delivering and implanting heart valve 300 will now be described with reference to FIGS. 4A-E. A delivery system 400 may be used to deliver and deploy heart valve 300 in native valve annulus 250A, and may generally include sheath 410, core 420, atraumatic tip 430 and hub 440. Sheath 410 may be slidable relative to core 420. Heart valve 300, including stent 306, valve assembly 308, legs 320 and sealing portion 322, may be disposed within sheath 410 about core 420 (FIG. 4A). Hub 440 may be coupled to core 420 and configured to mate with retaining elements 360 of heart valve 300. Elongated legs 320 of heart valve 300 may be disposed in the extended configuration of FIG. 3A, substantially parallel to sheath 410, during delivery. Specifically, though legs 320 are configured to return to their relaxed configuration by curling outwardly, they may be kept substantially linear by being constrained within sheath 410. By doing so, sealing portion 322 and legs 320 may be delivered to the native valve annulus using delivery system 400 without increasing the radius of sheath 410, avoiding the need to increase the crimp profile of the heart valve within delivery system 400. A large delivery system may be incapable of being passed through the patient's vasculature, while a delivery system having a heart valve with a smaller crimp profile may be easier to navigate through the patient's body and may also reduce the operation time. In the example shown in FIGS. 4A-E, delivery system 400 is delivered from the aorta toward the left ventricle as indicated by arrow S1. If heart valve 300 or delivery system 400 includes echogenic materials, such materials may be used to guide delivery system 400 to the appropriate position using the assistance of three-dimensional echocaradiography to visualize heart valve 300 within the patient. Alternative visualization techniques known in the art are also contemplated herein.

Figure 4B:
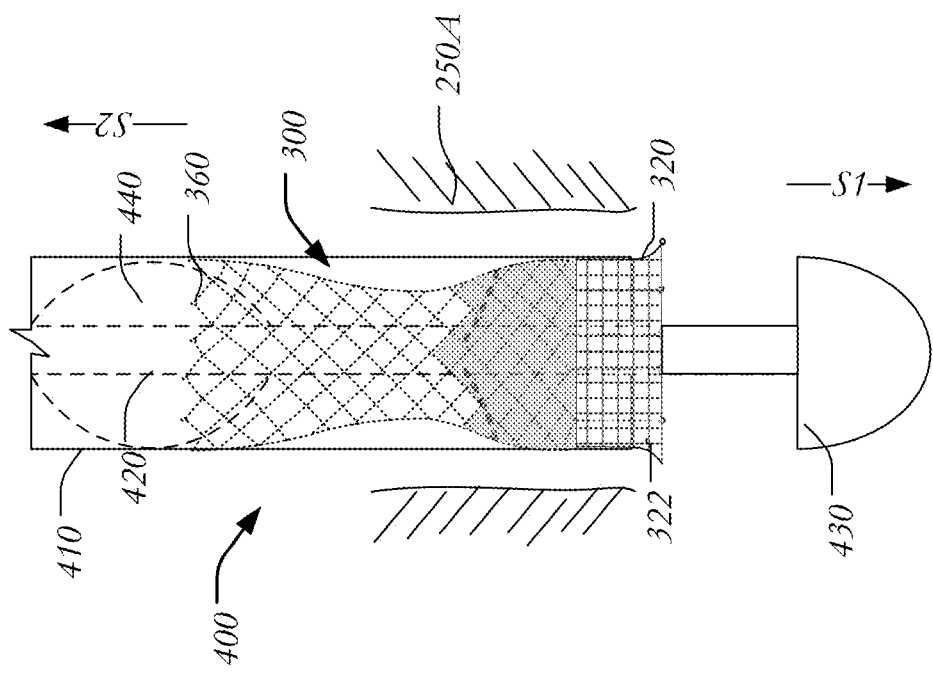
FIGS. 4A-E are highly schematic side views of one method of delivering and deploying the heart valve of FIGS. 3A and 3B within the native valve annulus.
Figure 4A:
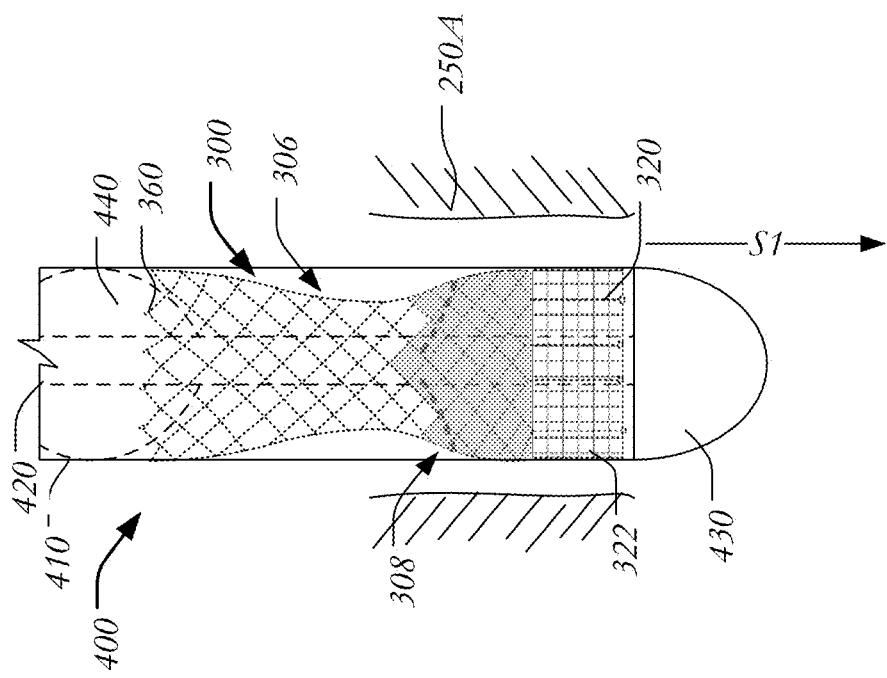
Figure 4C:
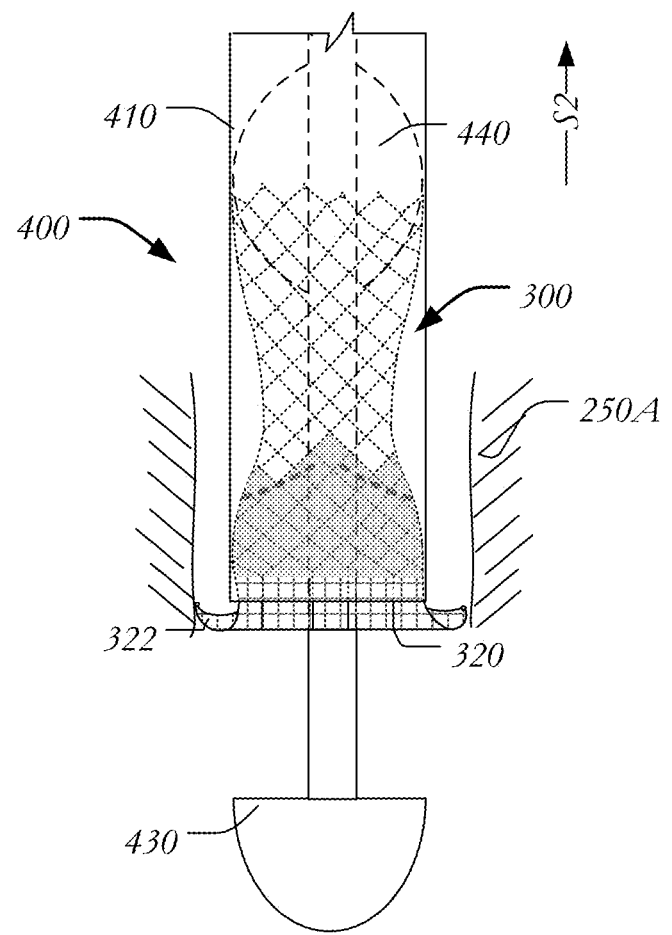
Figure 4E:
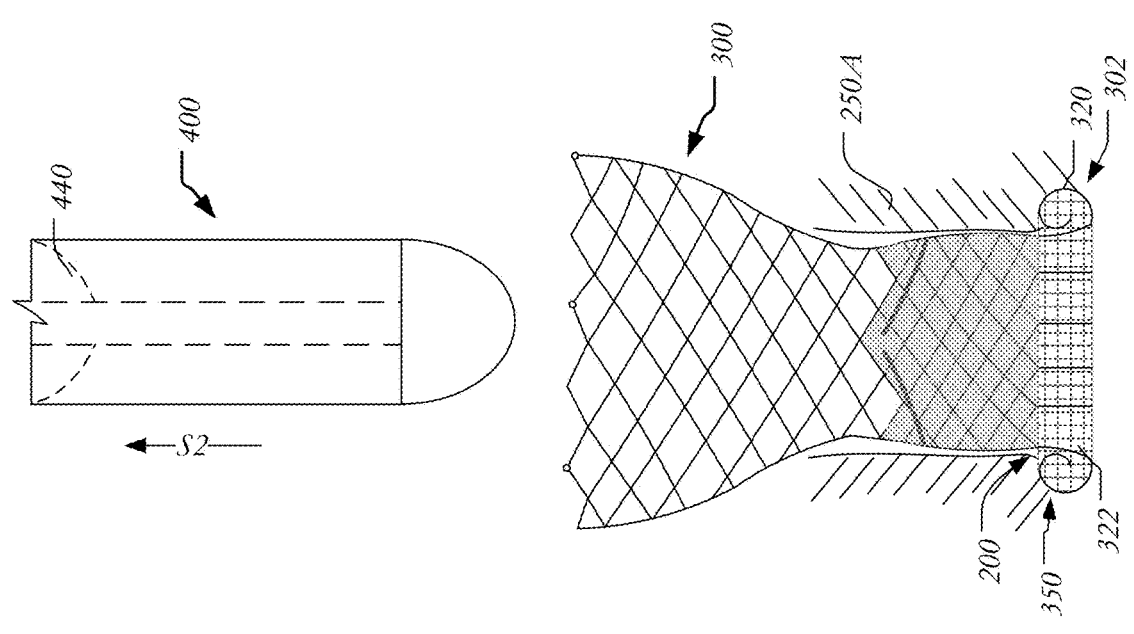
Figure 4D:
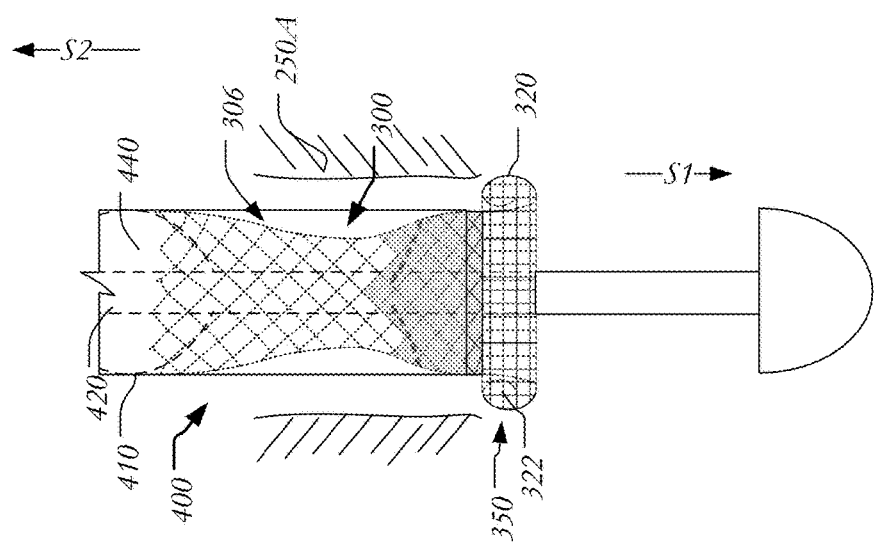

When delivery system 400 has reached the proper location (e.g. atraumatic tip 430 is just past native valve annulus 250A), atraumatic tip 430 may be advanced slightly in the direction of arrow S1 toward the left ventricle by pushing core 420 toward atraumatic tip 430 while holding sheath 410 in place which serves to decouple atraumatic tip 430 from sheath 410 (FIG. 4B). Sheath 410 may then be retracted in the direction of arrow S2 toward the aorta. As seen in FIG. 4B, with sheath 410 slightly retracted, legs 320 begin to emerge from the sheath and return to their relaxed configuration by curling outwardly with sealing portion 322, which is attached thereto, curling along with legs 320. As sheath 410 is further retracted in the direction of arrow S2, more of each leg 320 is exposed and curls upon itself (FIG. 4C) until legs 320 fully return to their relaxed configuration (FIG. 4D). Sealing portion 322 attached to curled legs 320 forms sealing ring 350. At this juncture, stent 306 is still disposed within sheath 410 and heart valve 300 has not yet begun to expand. Sheath 410 may be retracted further until heart valve 300 is free to self-expand within native valve annulus 250A. While heart valve 300 is partially deployed (e.g., a portion of heart valve 300 is outside sheath 410, but heart valve 300 is not fully detached from delivery system 400), if it appears that heart valve 300 needs to be recaptured and redeployed due to, for example, improper positioning or orientation, sheath 410 may be slid over core 420 in the direction of arrow S1 to recapture heart valve 300 within sheath 410. During recapture, sheath 410 may push against legs 320 to straighten them to the extended configuration shown in FIG. 4A. This process may be repeated until heart valve 300 is properly positioned and deployed within native valve annulus 250A. After sheath 410 has been fully retracted to expose heart valve 300, sealing ring 350, being disposed at proximal end 302 of heart valve 300, may occlude gaps 200 between heart valve 300 and native valve annulus 250A, thereby reducing or eliminating the amount of blood that passes around heart valve 300 through gaps 200 (FIG. 4E). Retaining elements 360 of heart valve 300 may be decoupled from hub 440 and delivery system 400, including atraumatic tip 430, may then be retracted through heart valve 300 in the direction of arrow S2 and removed from the patient.

Figure 5A:
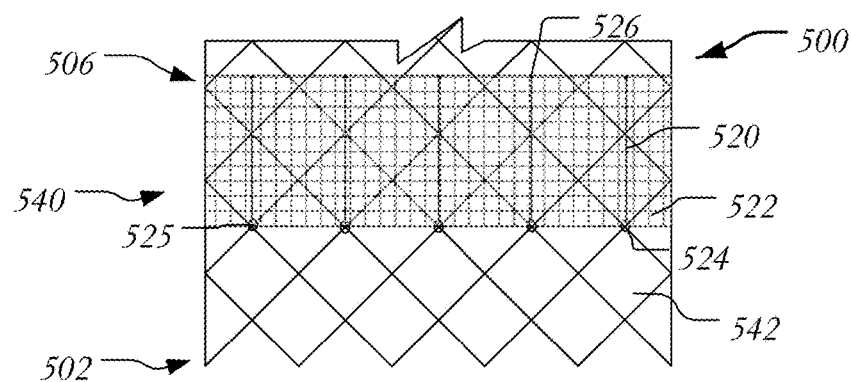
FIGS. 5A and 5B are enlarged highly schematic partial side views of another embodiment of a heart valve having a sealing portion disposed at the annulus section.
Figure 5B:
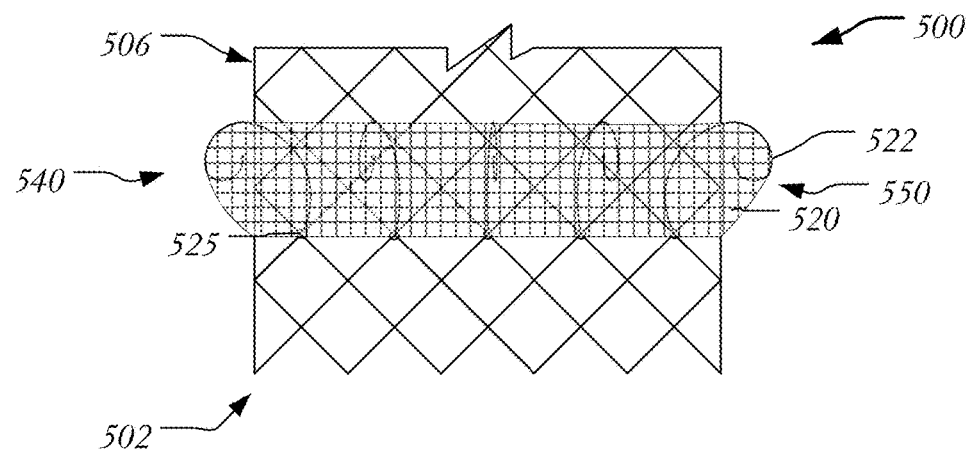

FIGS. 5A and 5B are enlarged schematic partial side views showing heart valve 500 having legs in an extended configuration and in a relaxed configuration, respectively. Heart valve 500 extends between proximal end 502 and a distal end (not shown) and generally includes stent 506 and a valve assembly (not shown for the sake of clarity) having a cuff and leaflets similar to those described above with reference to FIGS. 3A and 3B. Heart valve 500 further includes elongated legs 520 and sealing portion 522 attached to elongated legs 520 at eyelets 524 via sutures. These elements may be formed of any of the materials described above with reference to FIGS. 3A and 3B. Legs 520 may be attached to or formed integrally with stent 506 at attachment ends 525 to couple legs 520 to stent 506. As seen in FIG. 5A, legs 520 may be attached to stent 506 at eyelets 524 near the proximal end 502 of heart valve 500 at the top of the second row of cells 542 of stent 506, and in their extended configuration, may extend substantially linearly toward the distal end of the valve, terminating at free ends 526.

FIG. 5B illustrates the relaxed configuration of legs 520. Legs 520 may be biased so that, when they return to their relaxed configuration, they curl down toward the proximal end 502 of the valve. Due to the coupling of sealing portion 522 to legs 520, the curling of legs 520 results in a similar curling of sealing portion 522, causing it to roll down in the process to form upper sealing ring 550 within annulus portion 540 of heart valve 500. Upper sealing ring 550 may have a radius larger than that of the valve assembly, and therefore may be capable of filling any gaps between heart valve 500 and the native valve annulus (not shown). As shown in FIG. 5B, sealing ring 550 is spaced from proximal end 502 and may be useful for intra-leaflet applications that are described below with reference to FIG. 8A-C. In at least some examples, sealing ring 550 may be positioned within annulus portion 540 so as to be directly radially outward of the leaflets of heart valve 500 (not shown). Heart valve 500 may be disposed within a delivery system, delivered to the native valve annulus and deployed therein using a delivery system that is the same as or similar to that described in FIGS. 4A-E.

Alternatively, legs 520 may be attached to stent 506 at eyelets 524 and, in the extended condition, may extend substantially linearly toward the proximal end 502 of heart valve 500 so that free ends 526 are closer to proximal end 502 than attachment ends 525. In this alternative example, legs 520 may curl upward toward the distal end to form sealing ring 550. Thus, the location of attachment ends 525 and the direction of the curling of legs 520 may be used to vary the position of sealing ring 550 with respect to heart valve 500.

Figure 5C:
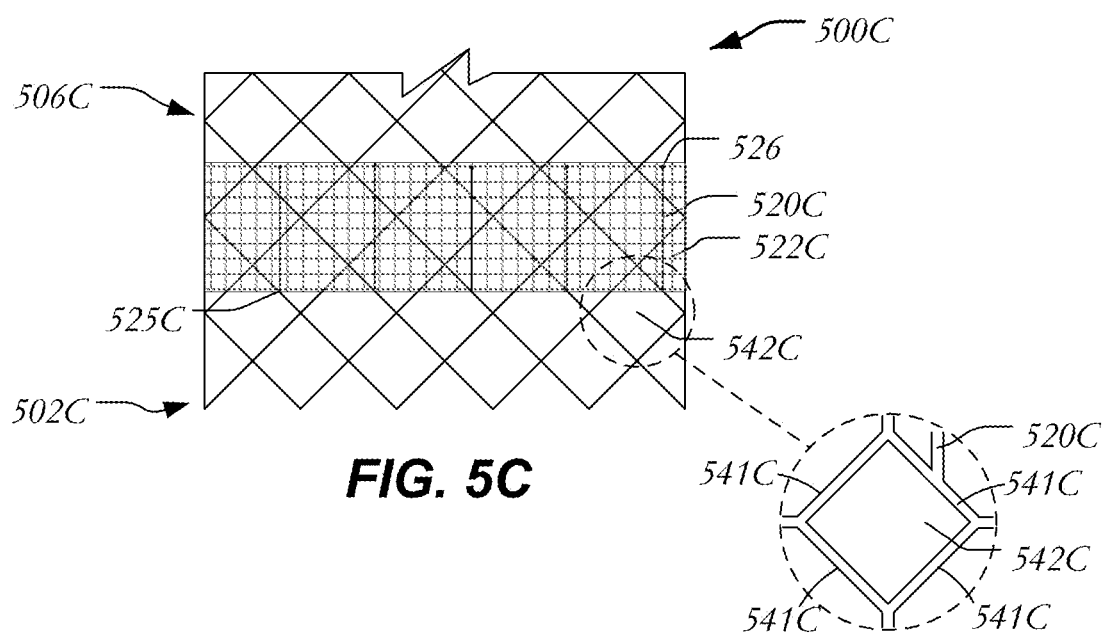
FIG. 5C is an enlarged highly schematic partial side view of another embodiment of a heart valve showing attachment ends of the elongated legs coupled to struts of a stent.

FIG. 5C is an enlarged schematic partial side view showing an alternate extended configuration of the elongated legs. Heart valve 500C extends between a proximal end 502C and a distal end (not shown) and generally includes stent 506C and a valve assembly (not shown for the sake of clarity) having a cuff and leaflets similar to those described above with reference to FIGS. 3A and 3B. Heart valve 500C further includes elongated legs 520C and sealing portion 522C attached to elongated legs 520C. These elements may be formed of any of the materials described above with reference to FIGS. 3A and 3B. Legs 520C may be attached to or formed integrally with stent 506C at attachment ends 525C to couple legs 520C to stent 506C. Specifically, legs 520C may be coupled to one or more struts 541C forming cells 542C or a portion of a cell. Though the previous embodiments have shown attachment ends 525C as being attached to or originating from an intersection of two struts 541C, attachment ends 525C may be coupled to or formed integrally with only one strut 541C. In this example, four struts 541C forming the four sides of cell 542C intersect at four corners of the cell, and attachment ends 525C are coupled to a single strut 541C approximately halfway between two corners of the cell. It will be understood, however, that elongated legs 520C may be coupled to any portion of stent 506C and/or to any location along struts 541C and/or to any number of struts. Elongated legs 520C may curl from a relaxed configuration in the same manners described above in connection with FIGS. 5A and 5B to form a sealing ring.

Figure 6A:
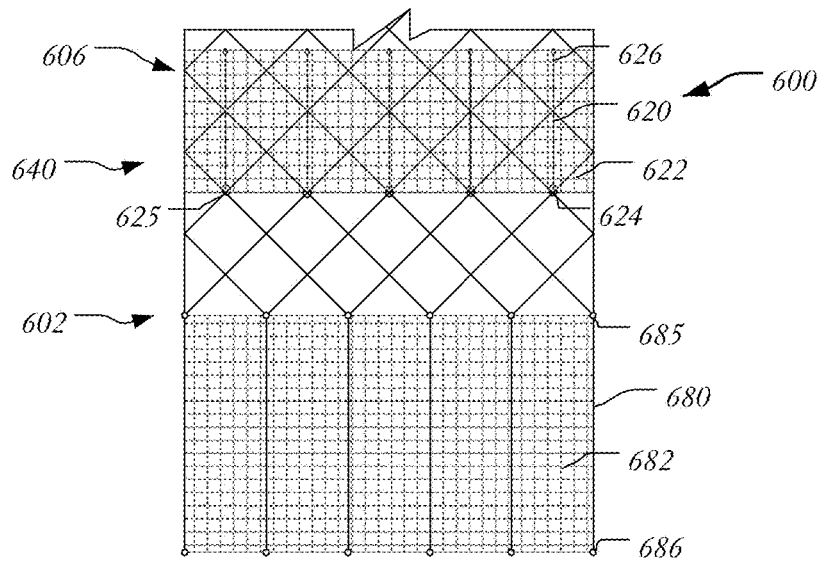
FIGS. 6A and 6B are enlarged highly schematic partial side views of another embodiment of a heart valve having multiple sealing portions.
Figure 6B:
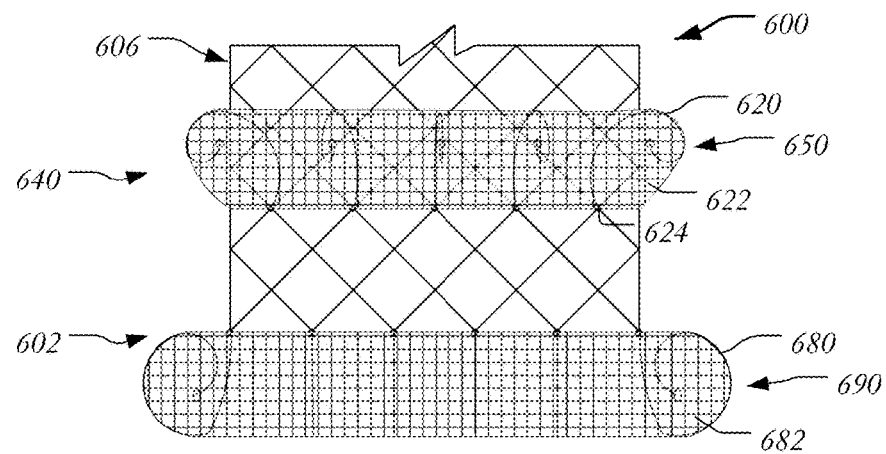

FIGS. 6A and 6B are schematic side views of another embodiment, showing heart valve 600 having legs in an extended configuration and a relaxed configuration, respectively. Heart valve 600 extends between proximal end 602 and a distal end (not shown) and generally includes stent 606 and a valve assembly (not shown for the sake of clarity) having a cuff and leaflets similar to those described above with reference to FIGS. 3A and 3B. Heart valve 600 further includes first elongated legs 620 and first sealing portion 622, which may be attached to first elongated legs 620 at eyelets 624 via sutures. In a configuration similar to that described above with reference to FIGS. 5A and 5B, first legs 620 may be attached to or formed integrally with stent 606 at attachment ends 625 near the proximal end 602 of heart valve 600, and may extend substantially linearly toward the distal end of the valve, terminating at free ends 626. Heart valve 600 further includes second elongated legs 680 attached to stent 606 at second attachment ends 685, which are located at proximal end 602 of the valve, and, in the extended condition, legs 680 extend substantially linearly away from the distal end of the valve to terminate at second free ends 686 beyond proximal end 602 of heart valve 600. A second sealing portion 682, similar to the sealing portion described above in connection with FIGS. 3A and 3B, may be attached to legs 680.

FIG. 6B illustrates the relaxed configuration of the legs of heart valve 600. First legs 620 may be biased so that, when they return to their relaxed configuration, they curl down toward the proximal end 602 of the valve, as shown in FIG. 6B. Due to the coupling of first sealing portion 622 to first legs 620, the curling of first legs 620 results in a similar curling of first sealing portion 622, causing it to roll down in the process to form upper sealing ring 650 within annulus portion 640 of heart valve 600 (e.g. forming a ring at an intra-leaflet position). Likewise, when secondary legs 680 return to their relaxed configuration, they may curl up toward the distal end of heart valve 600, pulling second sealing portion 682 with them to form lower sealing ring 690 (e.g., forming a ring at a sub-leaflet position). When heart valve 600 is implanted using a delivery system similar to that shown in FIGS. 4A-E, lower sealing ring 690 may take shape first as the outer sheath of the delivery system is retracted, followed by upper sealing ring 650. Additional methods may be used to actuate the formation of either of the sealing rings regardless of the delivery approach.

Figure 7A:
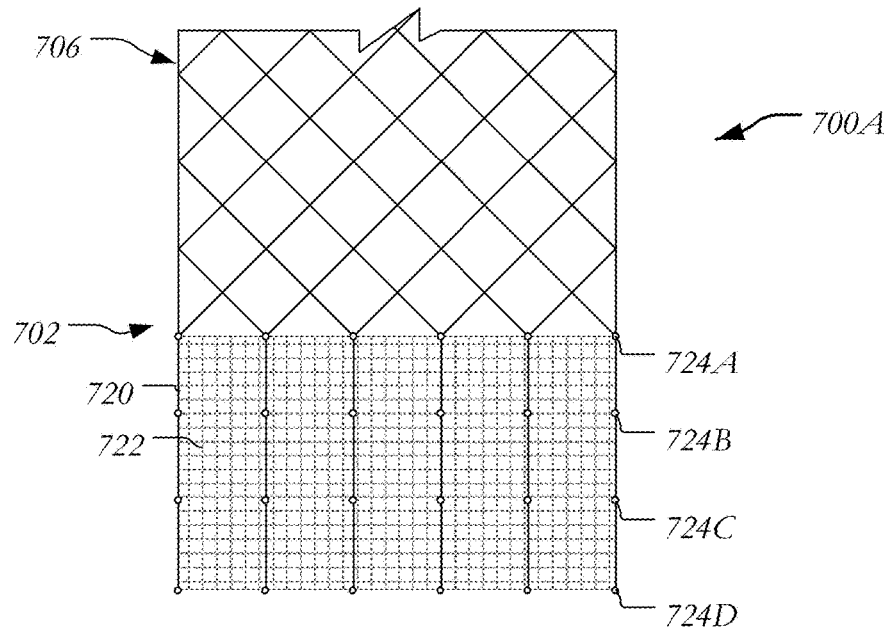
FIG. 7A is an enlarged highly schematic partial side view of another embodiment of a heart valve having elongated legs with multiple eyelets.

FIGS. 7A-D illustrate several additional variants of a heart valve having sealing portions according to the present disclosure. In FIG. 7A, heart valve 700A extends between proximal end 702 and a distal end (not shown) and generally includes stent 706 and a valve assembly (not shown) having a cuff and leaflets. Heart valve 700A further includes elongated legs 720 coupled to stent 706 near proximal end 702, which legs 720, in their extended configuration, may extend substantially linearly away from the distal end of the valve. A sealing portion 722 is coupled to legs 720. In order to provide a more secure attachment of sealing portion 722 to legs 720, each leg 720 may include multiple eyelets 724A-D along its length, and sealing portion 722 may be coupled to legs 720 at each of the eyelets. Eyelets 724A-D may be uniformly distributed along the length of each leg 720, as seen in FIG. 7A, resulting in better coupling of sealing portion 722 to legs 720 and a more uniform curling of sealing portion 722 in the formation of a sealing ring.

Figure 7B:
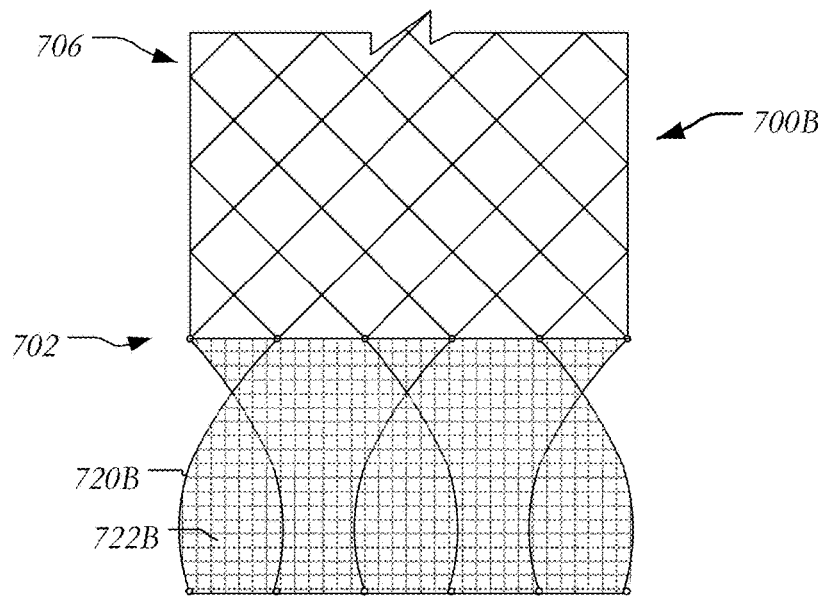
FIG. 7B is an enlarged highly schematic partial side view of another embodiment of a heart valve having wavy legs.

Although the elongated legs in all of the embodiments described above have a substantially linear configuration in the extended configuration, they may be formed with other configurations. FIG. 7B illustrates a heart valve 700B having nonlinear elongated legs. Heart valve 700B extends between proximal end 702 and a distal end (not shown) and includes stent 706 and a valve assembly having a cuff and leaflets as described above. Heart valve 700B includes elongated legs 720B that are curved or wavy in their extended configuration in contrast to the substantially linear legs of the previous embodiments. Wavy legs 720B may couple to stent 706 at proximal end 702 of heart valve 700B and extend away from the distal end thereof. Legs 720B may be formed to curl in their relaxed configuration in a manner similar to the elongated legs described above. A sealing portion 722B may be attached to legs 720B so as to form a sealing ring in the relaxed configuration of the legs.

Figure 7C:
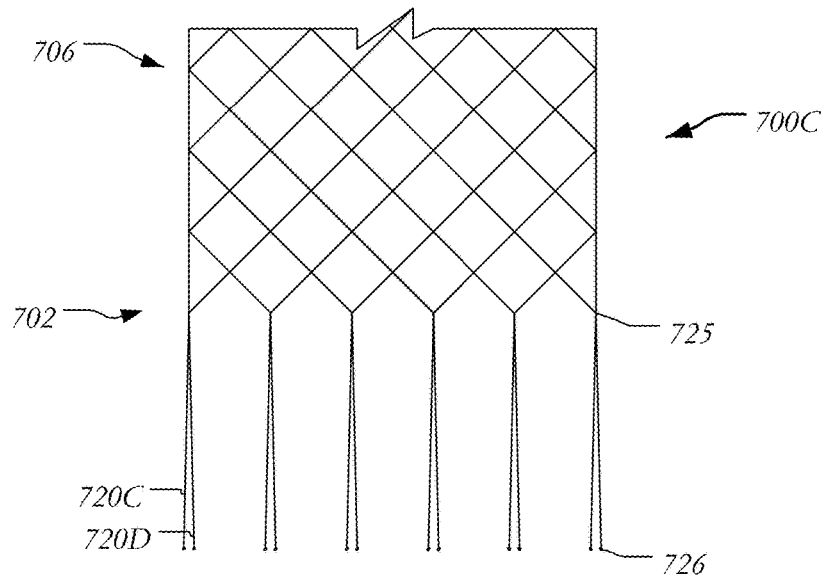
FIGS. 7C and 7D are enlarged highly schematic partial side views of another embodiment of a heart valve having pairs of elongated legs in the extended and relaxed configurations, respectively.
Figure 7D:
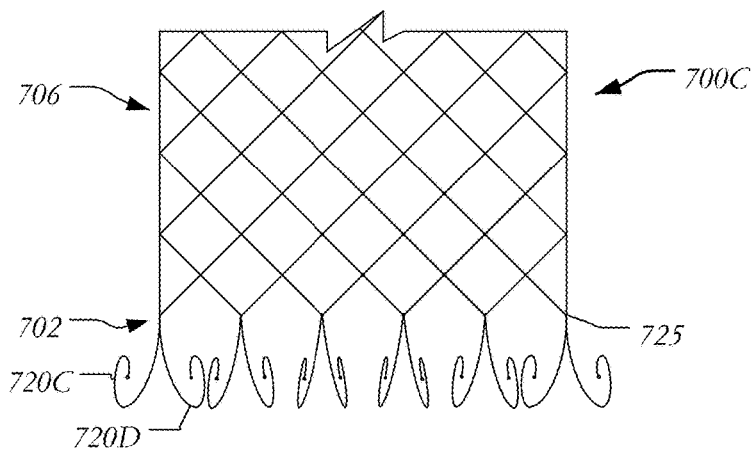

In FIGS. 7C and 7D, another example is shown in which heart valve 700C extends between a proximal end 702 and a distal end (not shown) and includes stent 706 and pairs of elongated legs 720C, 720D. Heart valve 700C further includes a valve assembly having a cuff and leaflets and a sealing portion (none of which are shown for the sake of clarity). In the extended configuration of the legs, shown in FIG. 7C, legs 720C, 720D are formed in pairs that originate at a common attachment end 725 at the apex of a cell at proximal end 702 and extend away from the distal end of heart valve 700C in substantially linear configurations to terminate in independent free ends 726. As shown in their relaxed configuration in FIG. 7D, legs 720C, 720D may curl upward toward the distal end of heart valve 700C along with the attached sealing portion, as previously described, to form a sealing ring. This configuration may provide additional structure for forming and supporting the sealing ring.

As will be appreciated from the embodiments described above, the elongated legs may be attached at the proximal end of a heart valve or anywhere in the annulus portion of the valve. Additionally, in their extended configuration, the elongated legs may extend either toward or away from the distal end of the heart valve, and in their relaxed configuration, may curl in either direction. By varying the points of attachment and the orientation of the elongated legs, sealing rings may be formed at different locations along the valve. In some applications, damaged or calcified native valve leaflets may not be resected prior to implantation of a prosthetic heart valve. The location of the sealing rings may be modified to accommodate the unresected native valve leaflets.

Figures 8A, 8B, 8C:
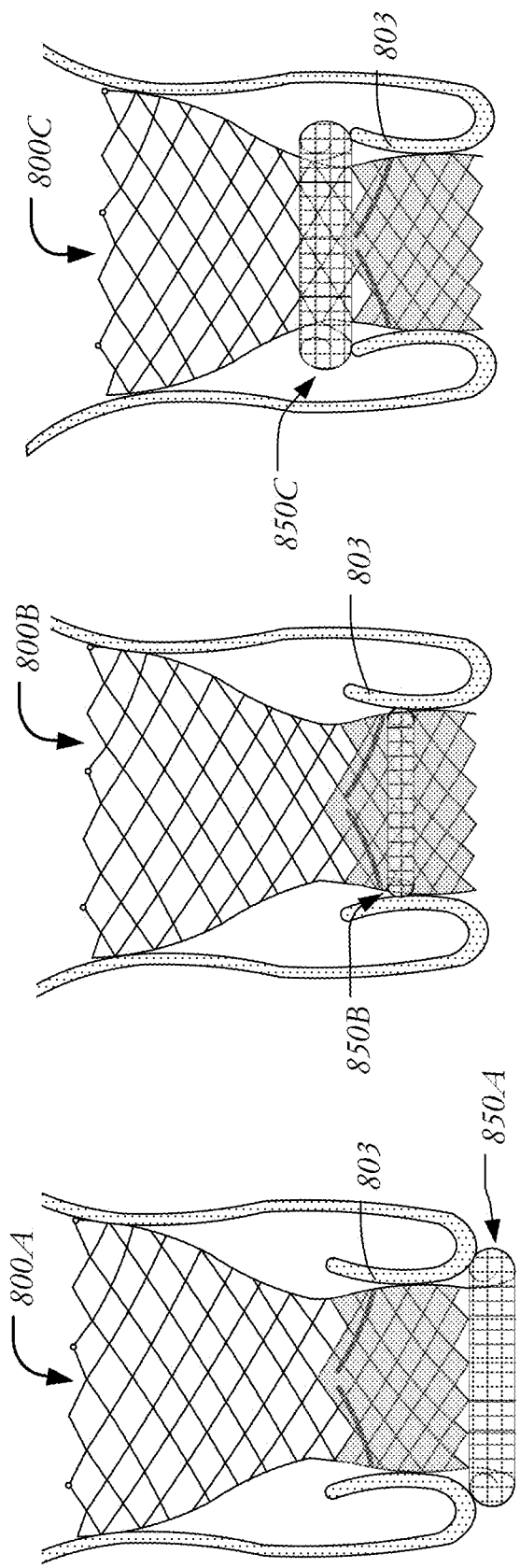
FIGS. 8A-C are highly schematic side views of heart valves having sealing rings disposed at various locations relative to the native leaflets.

FIGS. 8A-8C illustrate heart valves 800A-C disposed within a native valve annulus adjacent unresected native leaflets 803. In FIG. 8A, heart valve 800A includes sealing ring 850A at a proximal end thereof and configured to be disposed below native leaflets 803 (i.e., in a sub-leaflet location). Sealing ring 850A may be at least partially disposed below native leaflets 803 and may contact the native leaflets to provide a seal between heart valve 800A and native leaflets 803. FIG. 8B illustrates heart valve 800B having a sealing ring 850B spaced distally of the proximal end of the valve and configured to be disposed within native leaflets 803 to provide a seal between heart valve 800B and native leaflets 803 (i.e., in an intra-leaflet location). FIG. 8C illustrates a heart valve 800C having a sealing ring 850C spaced further distally of the proximal end of the valve and configured to be disposed above the free edges of native leaflets 803 to provide a seal between heart valve 800C and native leaflets 803 (i.e., in a supra-leaflet location). Thus, sealing rings 850A-C may be disposed at various locations relative to native leaflets 803. It will be appreciated that combinations of any of these sealing rings may be possible. For example, a heart valve may include two sealing rings, a first sealing ring 850A configured to be disposed below native leaflets 803, and a second sealing ring 850C configured to be disposed above the free edges of native leaflets 803. When sealing ring 850A is disposed below the native valve leaflets 803 (FIG. 8A), it may prevent heart valve 800A from migrating into the aorta. When sealing ring 850C is disposed above the native valve leaflets (FIG. 8C), it may prevent heart valve 800C from migrating into the left ventricle. Thus, with this and similar configurations, sealing rings may be used to anchor a heart valve in the native valve annulus, thereby preventing the heart valve from migrating from its intended position.

Figure 9A:
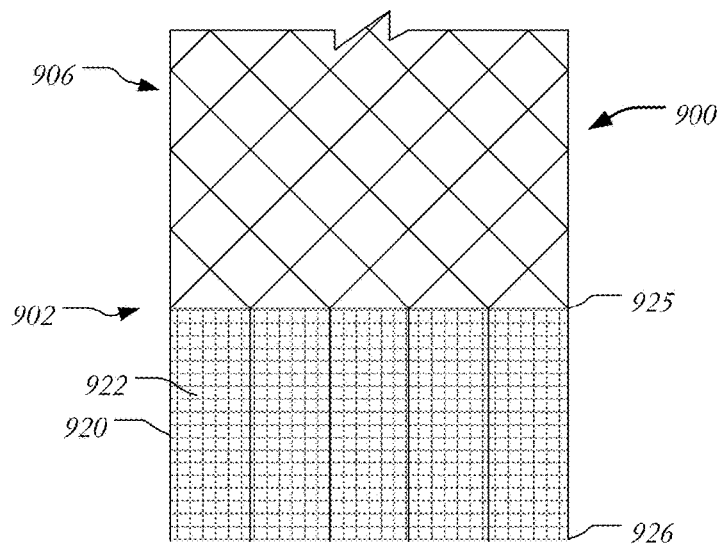
FIGS. 9A and 9B are enlarged highly schematic partial side views of another embodiment of a heart valve having elongated legs in the extended and relaxed configurations, respectively.
Figure 9C:
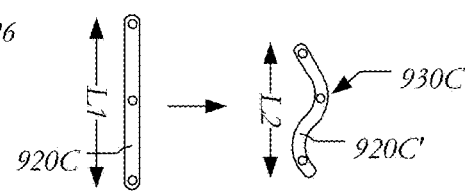
FIGS. 9C and 9D are examples of the shortening of an elongated leg from the extended configuration of FIG. 9A to the relaxed configuration of FIG. 9B.
Figure 9B:
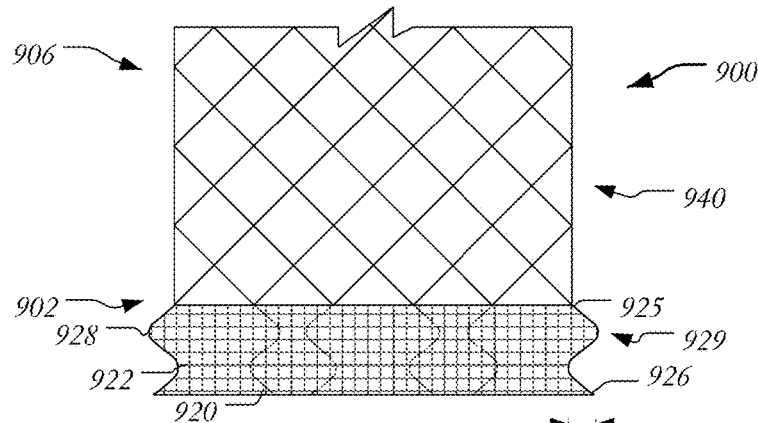

FIGS. 9A and 9B illustrate a heart valve 900 pursuant to another embodiment having sealing features to mitigate perivalvular leakage. Heart valve 900 of FIG. 9A extends between a proximal end 902 and a distal end (not shown) and includes a stent 906, a valve assembly (not shown) including a cuff and leaflets, and elongated legs 920. Legs 920 may be attached to stent 906 at attachment ends 925 near the proximal end 902 of heart valve 900 and, in the extended configuration of the legs shown in FIG. 9A, may extend substantially linearly away from the distal end of the valve, terminating in free ends 926. A sealing portion 922 may be attached to legs 920 in the same manner as the sealing portions described above. When legs 920 of heart valve 900 return to their relaxed configuration, instead of curling over themselves as shown in the previous embodiments, they may axially collapse to form an undulating shape, as seen in FIG. 9B. As a result of this collapse, portions of legs 920 may billow radially out from the profile of the annulus portion 940 of heart valve 900 by an additional distance $d_1$ to form distended portion 928. As shown in FIG. 9B, multiple distended portions 928 may be formed. Each distended portion 928 may extend circumferentially to form a sealing ring 929 or a portion of a sealing ring.

Figure 9D:
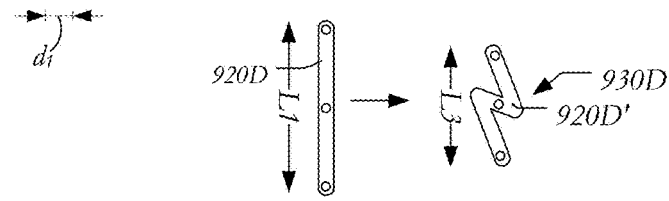

FIG. 9C illustrates a first example of an elongated leg 920C that is capable of collapsing axially to form distended portion 928. In this first example, leg 920C may be substantially linear and have a first length L1 in an extended configuration. Leg 920C may be heat set or otherwise configured to axially collapse to an undulating shape 920C' having a shorter length L2 in the relaxed configuration. When leg 920C assumes undulating shape 920C' it will not only shorten, but will also form convex regions 930C along its length that collectively define distended portions 928 of sealing ring 929. FIG. 9D illustrates another example in which an elongated leg 920D having a length L1 in an extended configuration shortens to an N-shape 920D' having a length L3 in the relaxed configuration. Legs 920D form convex regions 930D along their lengths that collectively define distended portions 928 of heart valve 900. It will be understood that FIGS. 9C and 9D illustrate only two possible examples for forming distended portions 928 and that various techniques and shapes may be used to alternate between a substantially linear elongated leg in the extended configuration and a shortened shape having convex regions in the relaxed configuration.

Figure 10A:
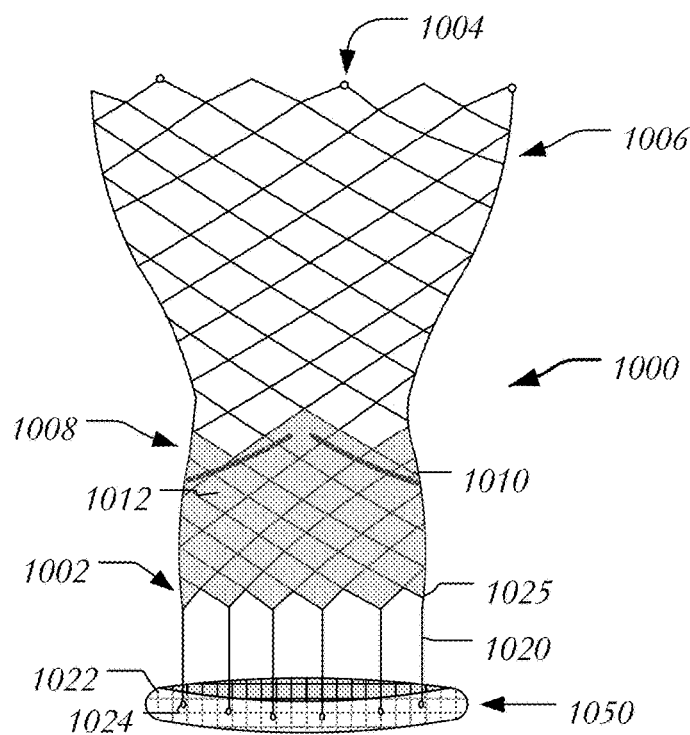
FIGS. 10A and 10B are highly schematic side views of another embodiment of a heart valve having a sealing ring intended to fill irregularities between the heart valve and the native valve annulus.
Figure 10B:
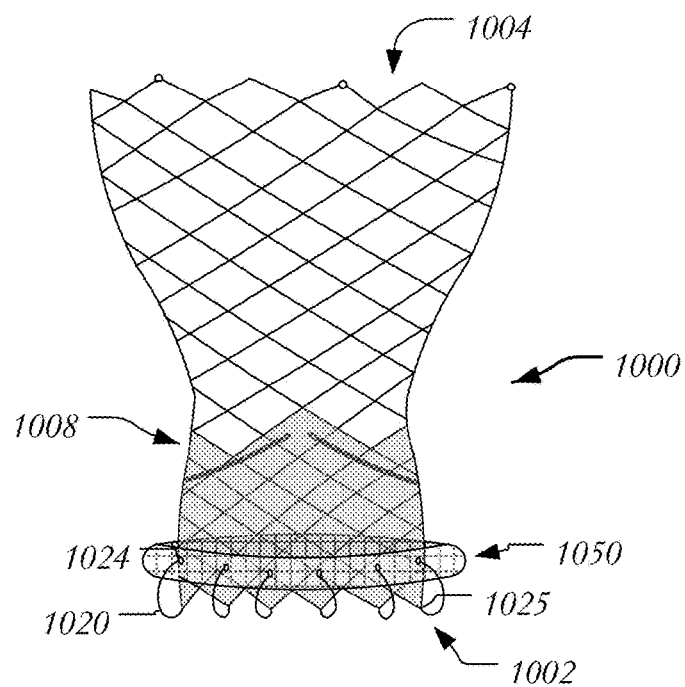

FIGS. 10A and 10B illustrate a heart valve 1000 in accordance with another embodiment. Heart valve 1000 extends between proximal end 1002 and distal end 1004, and may generally include stent 1006 and valve assembly 1008 having a plurality of leaflets 1010 and cuff 1012. Additionally, heart valve 1000 may include a number of elongated legs 1020 and a sealing portion 1022 coupled to the elongated legs via eyelets 1024 to mitigate perivalvular leakage. Legs 1020 may be formed of a shape memory material such as those described above with reference to FIGS. 3A and 3B and may have an extended configuration and a relaxed configuration. Attachment ends 1025 of elongated legs 1020 may be affixed to stent 1006 near proximal end 1002 of heart valve 1000, and legs 1020 may extend away from the distal end 1004 of stent 1006 and terminate at eyelets 1024. In this example, sealing portion 1022 may be in the form of a generally toroidal-shaped sealing ring 1050, regardless of whether legs 1020 are in their extended or relaxed configuration. As used herein, the terms "toroid" and "toroidal" are not limited to a circle revolved about an axis external to the circle, which is parallel to the plane of the figure and does not intersect the figure, but also include the revolving of other plane geometrical figures such as, for example, an oval, a triangle, a square and the like. Sealing ring 1050 may be formed of a braided fabric comprising a plurality of braided strands, although it will be understood that any of the other materials described above with reference to FIGS. 3A and 3B may be used as well. In the extended configuration of legs 1020, sealing ring 1050 may be spaced away from proximal end 1002 by the length of the legs.

As noted above, legs 1020 may have an extended configuration and a relaxed configuration. FIG. 10B illustrates the relaxed configuration. When legs 1020 of heart valve 1000 are permitted to return to their relaxed configuration, they may curl up toward distal end 1004 and pull sealing ring 1050 over proximal end 1002 of heart valve 1000 so that sealing ring 1050 is at least partially disposed over valve assembly 1008 and/or cuff 1012. Sealing ring 1050 may have a radius larger than that of valve assembly 1008, the larger radius of sealing ring 1050 being capable of filling any gaps between heart valve 1000 and the native valve annulus (not shown). Thus, in this embodiment, sealing ring 1050 is already formed in both the extended and relaxed configurations of legs 1020, but is brought into place for sealing when legs 1020 curl upward in the relaxed configuration.

Figure 10C:
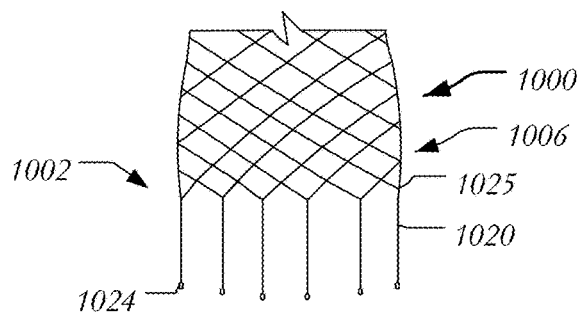
FIGS. 10C-E are highly schematic partial side views of elongated legs in a stretched configuration and two variations of bending the elongated legs.
Figure 10D:
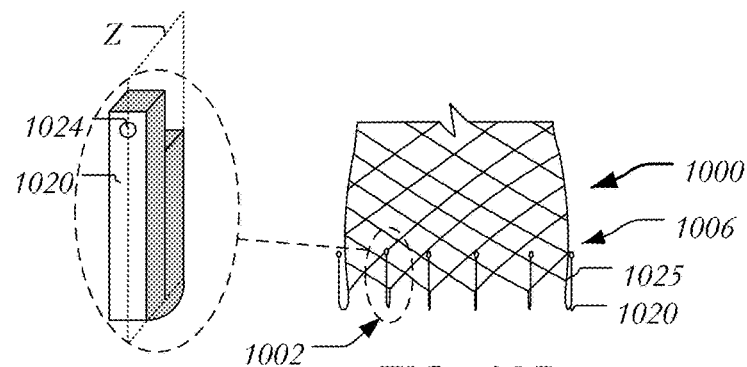
Figure 10E:
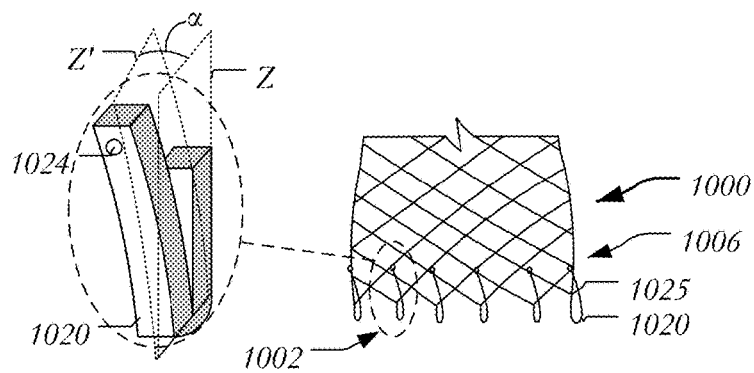

FIGS. 10C-E illustrate the extended configuration of legs 1020 and two examples of the relaxed configuration of legs 1020. As seen in FIG. 10C, in the extended configuration, legs 1020 are coupled to stent 1006 of heart valve 1000 near proximal end 1002 and are substantially linear between eyelets 1024 and attachment ends 1025. In one example shown in FIG. 10D, elongated legs 1020 are configured to curl toward the distal end (not shown) of heart valve 1000, each elongated leg 1020 being bent straight back so that substantially the entire leg lies in a single plane Z. Alternatively, as shown in FIG. 10E, each elongated leg 1020 may also be bent with respect to the plane of attachment Z such that it ends in a second plane Z' which forms an angle α with respect to plane of attachment Z. The angle between the two planes may be between about 1 degree and about 60 degrees. By bending leg 1020 in such a manner, leg 1020 may be more conformable, aiding in the transition between the extended and the relaxed configurations.

Figure 10F:
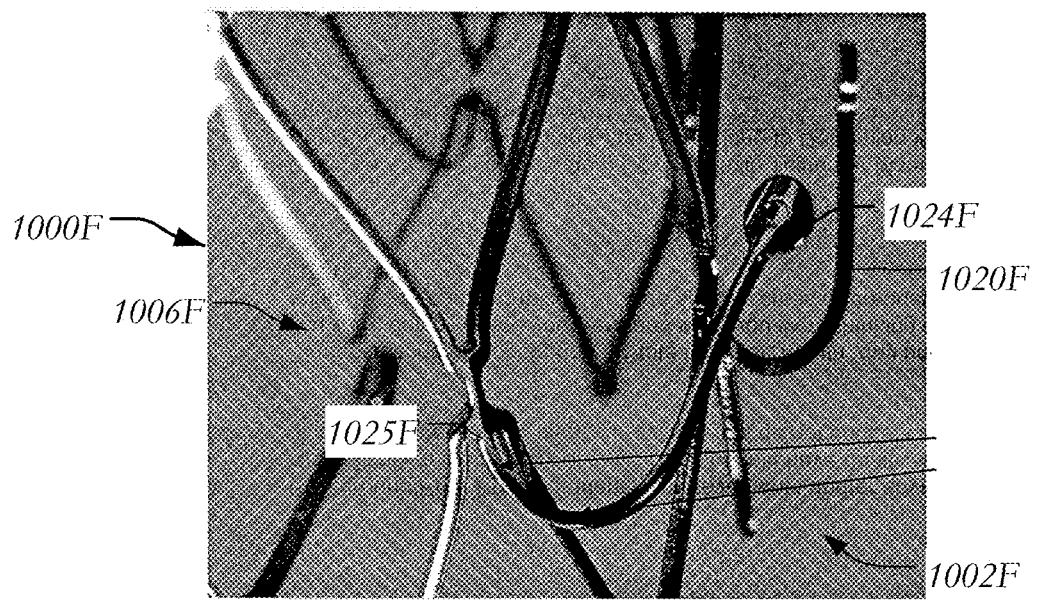
FIG. 10F is an enlarged partial perspective view of the bending of the elongated legs.

FIG. 10F is an enlarged partial perspective view showing the bending of the elongated legs of heart valve 1000F. Heart valve 1000F may extend between a proximal end 1002F and a distal end (not shown) and includes stent 1006F and elongated legs 1020F, each having an eyelet 1024F. Elongated legs 1020F may be coupled to stent 1006F at attachment ends 1025F. It may be difficult to bend elongated legs 1020F due to the thickness and width of the legs. Elongated legs 1020F therefore may be twisted along their longitudinal axes in order to more easily bend the legs. In addition to twisting, elongated legs 1020F may be bent as described above with reference to FIG. 10E. The twisting and bending of elongated legs 1020 may weaken the legs so that a desired stiffness is achieved for proper extension and relaxation of the legs.

Figure 11A:
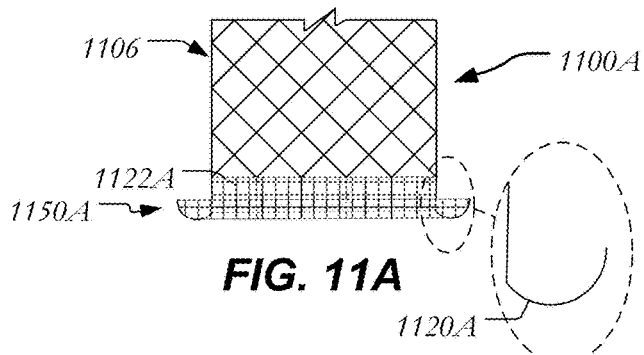
FIGS. 11A-F are highly schematic partial side views of a heart valve showing variations of bending the elongated legs.
Figure 11B:
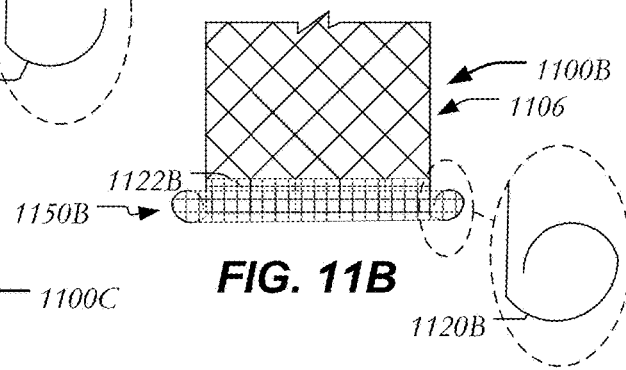
Figure 11C:
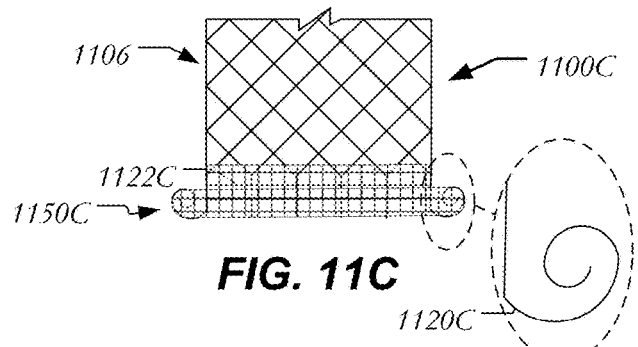
Figure 11D:
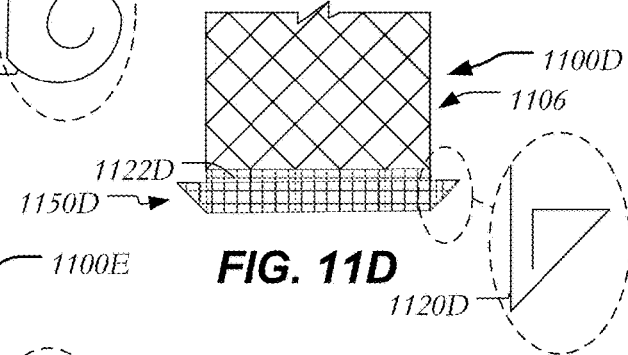

FIGS. 11A-F are highly schematic partial side views of heart valves, showing variations in how the elongated legs are bent in the relaxed configuration. In a first example, heart valve 1100A includes stent 1106 and elongated legs 1120A coupled thereto (FIG. 11A). Elongated legs 1120A of heart valve 1100A bend in the shape of a semicircle, and sealing portion 1122A, which is attached to elongated legs 1120A, curls with the elongated legs to form a sealing ring 1150A in the shape of a semicircle revolved about an axis external to the semicircle, which is parallel to the plane of the figure and does not intersect the figure. In a second example, heart valve 1100B includes stent 1106 and elongated legs 1120B coupled thereto (FIG. 11B). Elongated legs 1120B of heart valve 1100B bend to form an almost complete circle, and sealing portion 1122B, which is attached to elongated legs 1120B, curls with the elongated legs to form a sealing ring 1150B in the shape of an ellipsoid revolved in the manner described above. FIG. 11C illustrates another example in which heart valve 1100C includes stent 1106 and elongated legs 1120C, which bend in multiple curls to form sealing portion 1122C into a spiral-shaped sealing ring 1150C in the shape of a revolved curl. It will be understood from these examples that the elongated legs may include any number of curls or portions of curls.

Figure 11E:
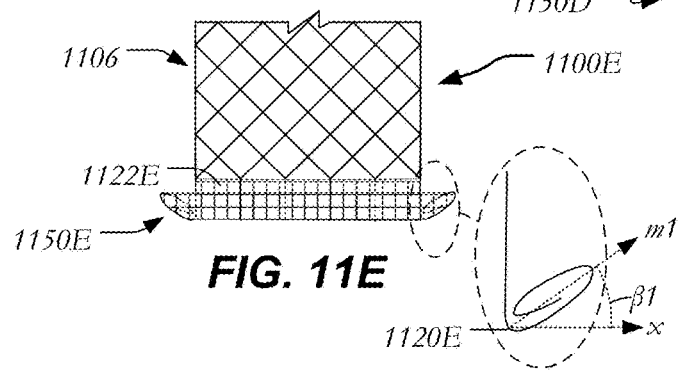
Figure 11F:
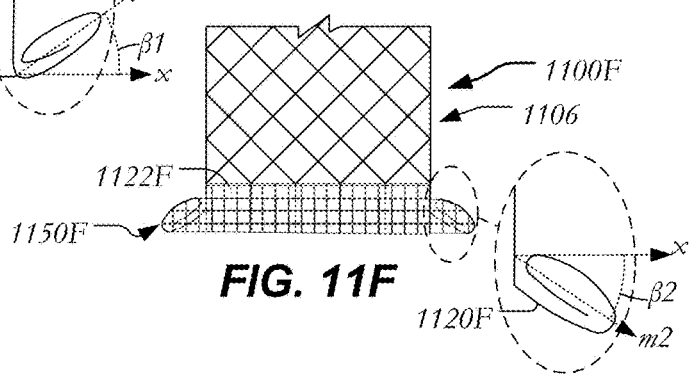

Moreover, the elongated legs may take a number of shapes other than curls. For example, in FIG. 11D, heart valve 1100D includes elongated legs 1120D coupled to stent 1106. Elongated legs 1120D are configured to bend in the shape of a triangle as shown, sealing portion 1122D bending with them to form sealing ring 1150D in the shape of a revolved triangle. FIG. 11E illustrates another example of heart valve 1100E having elongated legs 1120E coupled to stent 1106. Elongated legs 1120E curl in a substantially elliptical shape having a major axis m1 disposed at an upward angle $\beta 1$ with respect to an axis x extending in the radial direction of heart valve 1100E. In this example, major axis m1 forms an upward angle $\beta 1$ of about 40 degrees with respect to axis x, causing sealing portion 1122E to form sealing ring 1150E in the shape of a distally-pointing revolved ellipsoid. In an alternative configuration, elongated legs 1120F may be coupled to stent 1106 of heart valve 1100F as shown in FIG. 11F. Elongated legs 1120F curl in a substantially elliptical shape as in FIG. 11E, the ellipse having a major axis m2 disposed at a downward angle $\beta 2$ with respect to an axis x extending in the radial direction of heart valve 1100F. In this example, major axis m2 forms a downward angle $\beta 2$ of about 40 degrees with respect to axis x, causing sealing portion 1122F to form sealing ring 1150F in the shape of a proximally-pointing revolved ellipsoid. It will be understood that various modifications may be made to any of these basic shapes of the elongated legs. For example, the foregoing shapes may be inverted when the elongated legs extend toward the distal end of a heart valve (e.g., a triangle that is inverted from that shown in FIG. 11D). Thus, the elongated legs may take any desired shape to form sealing rings of various profiles and radiuses to adequately seal the region between the heart valve and the native valve annulus.

Figure 12:
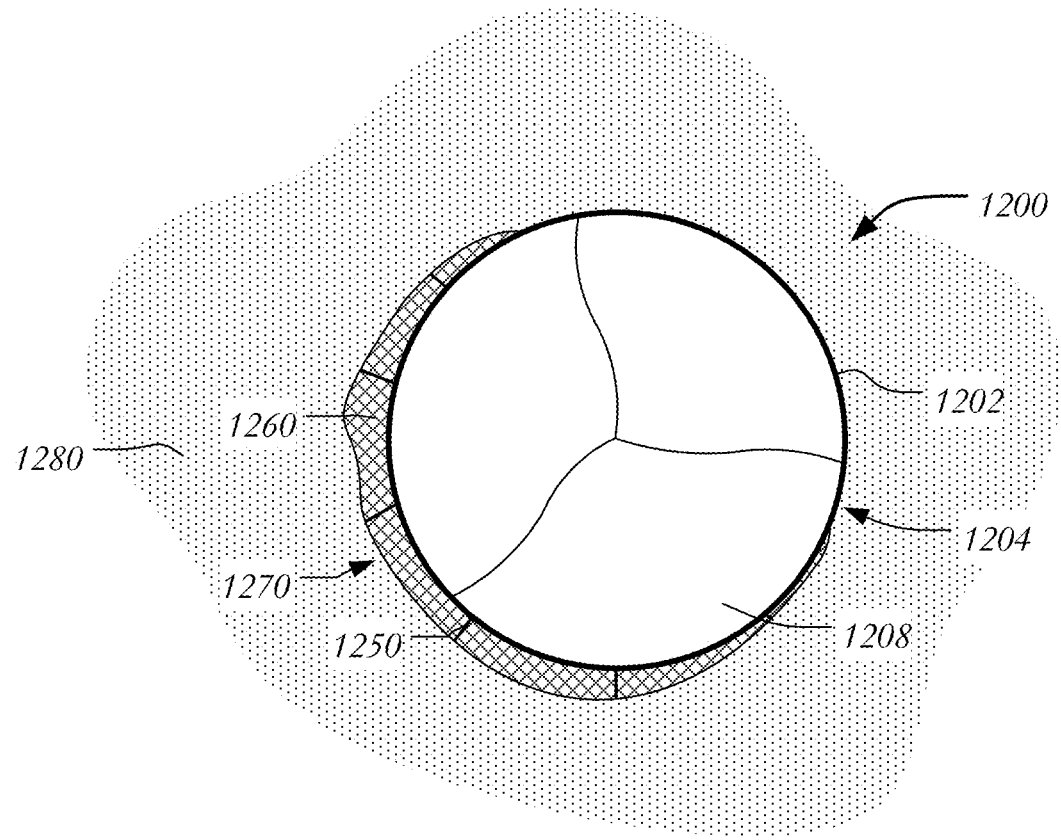
FIG. 12 is a highly schematic cross-sectional view showing a prosthetic heart valve disposed within a native valve annulus and having a sealing ring in its fully expanded state.

FIG. 12 is a highly schematic cross-sectional view showing heart valve 1200 having stent 1202, valve assembly 1204 including a cuff (not shown) and leaflets 1208, and elongated legs 1250 supporting a sealing portion 1260. Legs 1250 have curled up to form sealing ring 1270 and heart valve 1200 has been disposed within native valve annulus 1280. As seen in FIG. 12, sealing ring 1270 has radially expanded to fill gaps 200 shown in FIG. 2, and may be capable of promoting tissue growth between heart valve 1200 and native valve annulus 1280. For example, sealing portion 1260 may be innately capable of promoting tissue growth and/or may be treated with a biological or chemical agent to promote tissue growth, further enabling sealing ring 1270, when expanded, to seal the heart valve within the native valve annulus. Alternatively, the expanded sealing ring 1270 may be sufficiently dense to adequately seal around heart valve 1200 without the need for major tissue growth. Sealing portion 1260 may also be double-layered and in embodiments having a mesh sealing portion, it may include tighter braiding to more completely occlude the space between heart valve 1200 and native valve annulus 1280. When sealing ring 1270 is functioning properly, heart valve 1200 will be adequately sealed within native valve annulus 1280 so that blood flows through leaflets 1208 of valve assembly 1204, and so that blood flow through any gaps formed between heart valve 1200 and native valve annulus 1280 is limited or reduced.

Figure 13A:
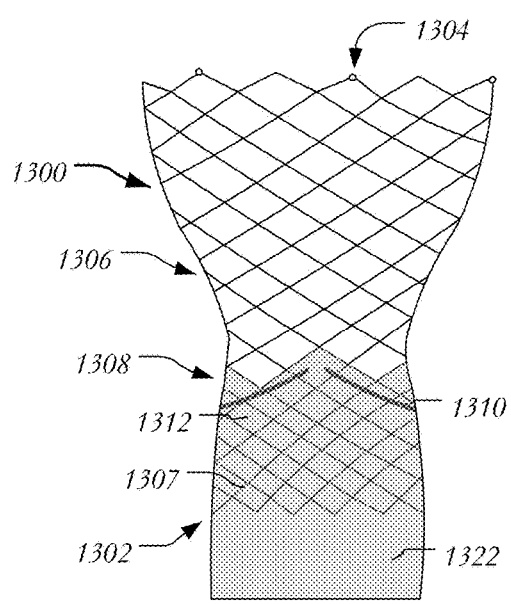
FIGS. 13A and 13B are highly schematic side views of another embodiment of a heart valve having a sealing ring intended to fill irregularities between the heart valve and the native valve annulus.
Figure 13B:
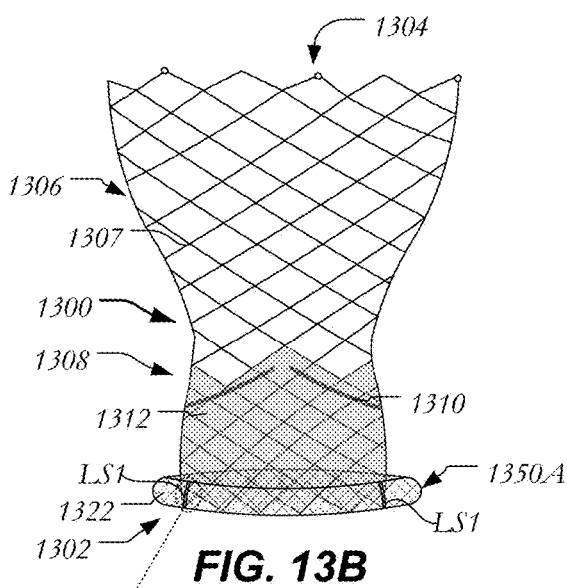
Figure 13C:
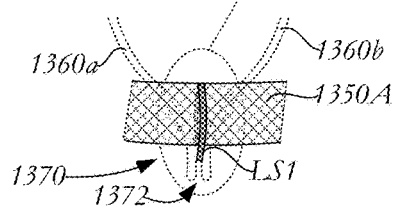
FIG. 13C is a schematic end view of the prosthetic heart valve of FIGS. 13A and 13B after formation of a sealing ring as seen from the annulus end toward the aortic end of the heart valve.
Figure 13C:
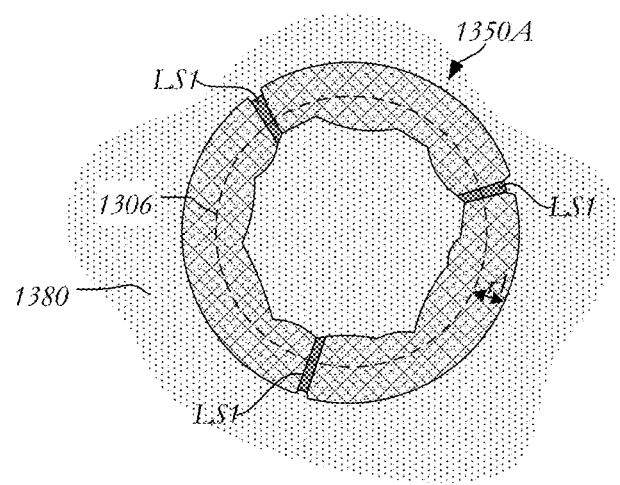

FIGS. 13A-C illustrate a heart valve 1300 in accordance with another embodiment. Heart valve 1300 extends between proximal end 1302 and distal end 1304, and may generally include stent 1306 formed of a plurality of struts 1307, and valve assembly 1308 having a plurality of leaflets 1310 and a cuff 1312. Cuff 1312 may include surplus portion 1322 that extends past the most-proximal struts 1307 of stent 1306. In some examples, surplus portion 1322 may longitudinally extend between about 10 mm and about 20 mm proximally from the most-proximal struts 1307 of stent 1306. Surplus portion 1322 may be formed of the same material as the rest of cuff 1312 and may be formed integrally therewith from a single piece of material. Alternatively, surplus portion 1322 may be formed of a different material than cuff 1312 that is sutured, glued or otherwise affixed to the proximal end of cuff 1312.

FIG. 13B illustrates heart valve 1300 after surplus portion 1322 has been rolled to form sealing ring 1350A. After assembly of cuff 1312 to stent 1306, surplus portion 1322 may be rolled in the direction of distal end 1304 until it is aligned with the proximal-most struts 1307 to form sealing ring 1350A. In this example, surplus portion 1322 is rolled into a generally toroidal-shaped sealing ring 1350A near proximal end 1302 of heart valve 1300 (e.g., at a subannular position). Sealing ring 1350A may be formed of one complete revolution of surplus portion 1322, or of a series of revolutions (e.g., two, three or more revolutions of surplus portion 1322).

Sealing ring 1350A may maintain its shape through a variety of methods, such as by being tied to select struts 1307 of stent 1306. In one example, as seen in the enlarged schematic view of FIG. 13B, end struts 1360a and 1360b of stent 1306 meet to form a horseshoe-shaped end 1370 having a partial slot 1372 therebetween. A number of locking stitches LS1 may be tied around horseshoe-shaped ends 1370, and specifically around each slot 1372 and sealing ring 1350A to keep the sealing ring from unfurling. Locking stitches LS1 may be formed of a suture, string or any other suitable biocompatible thread. It will be understood that, though three locking stitches are shown around the circumference of the heart valve to couple sealing ring 1350A to stent 1306, any number of locking stitches may be used. Other techniques for maintaining the shape of sealing ring 1350A may also be used including adhesive, glue or the like. Sealing ring 1350A may have a radius larger than that of valve assembly 1308, the larger radius of sealing ring 1350A being capable of filling any gaps between heart valve 1300 and the native valve annulus (not shown).

FIG. 13C illustrates prosthetic heart valve 1300 in native valve annulus 1380 after formation of sealing ring 1350A as seen from proximal end 1302 (e.g., as seen from the annulus end toward the aortic end of the heart valve). Sealing ring 1350A has been secured to stent 1306 via a series of locking stitches LS1. The outer diameter of stent 1306 at the proximal end is indicated with a dashed-line. Sealing ring 1350A extends radially outward from the outer diameter of stent 1306 at the proximal end of heart valve 1300 by a radial distance r1. In at least some examples, radial distance r1 may be between about 1 mm and about 2.5 mm.

Figure 13D:
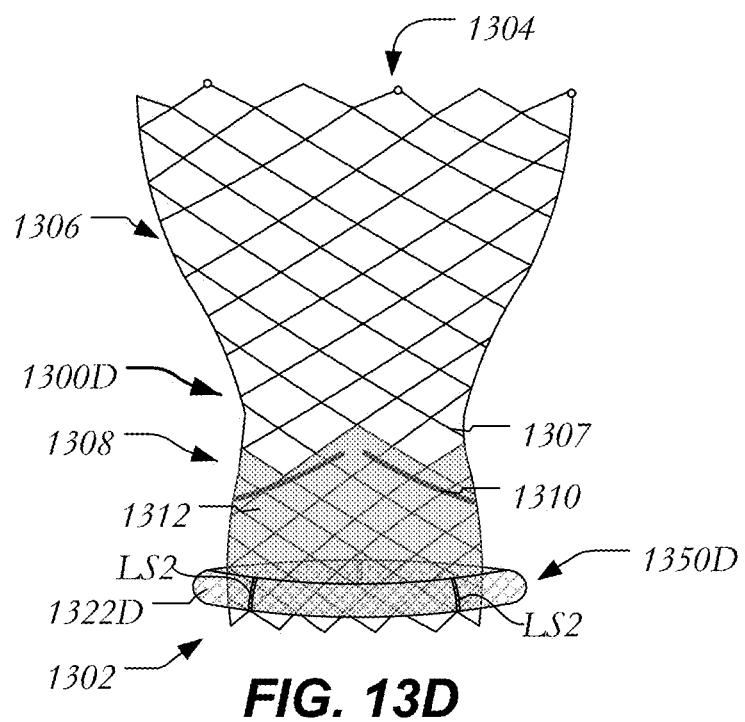
FIG. 13D is a highly schematic side view of a variation of the embodiment shown in FIGS. 13A-C.

FIG. 13D illustrates heart valve 1300D, which is a variant of heart valve 1300 of FIGS. 13A-C. Heart valve 1300D extends between proximal end 1302 and distal end 1304, and may generally include stent 1306 formed of struts 1307, and valve assembly 1308 having a plurality of leaflets 1310 and a cuff 1312. A surplus portion 1322D of cuff 1312 has been rolled to form sealing ring 1350D in a manner similar to that described above, except that sealing ring 1350D has been rolled to a position closer to distal end 1304 and leaflets 1310 than sealing ring 1350A (e.g., at an intra-annular position). After rolling surplus portion 1322D and forming sealing ring 1350D at the appropriate position, locking stitches LS2 may be coupled to sealing ring 1350D and select struts 1307 of stent 1306 to secure the sealing ring in place.

Figure 14A:
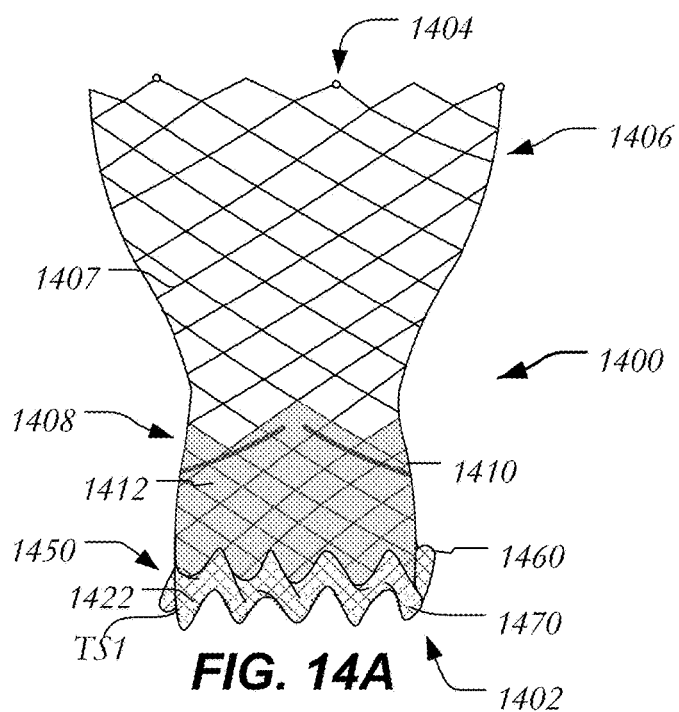
FIG. 14A is a highly schematic side view of another embodiment of a heart valve having an undulating sealing ring intended to fill irregularities between the heart valve and the native valve annulus.
Figure 14B:
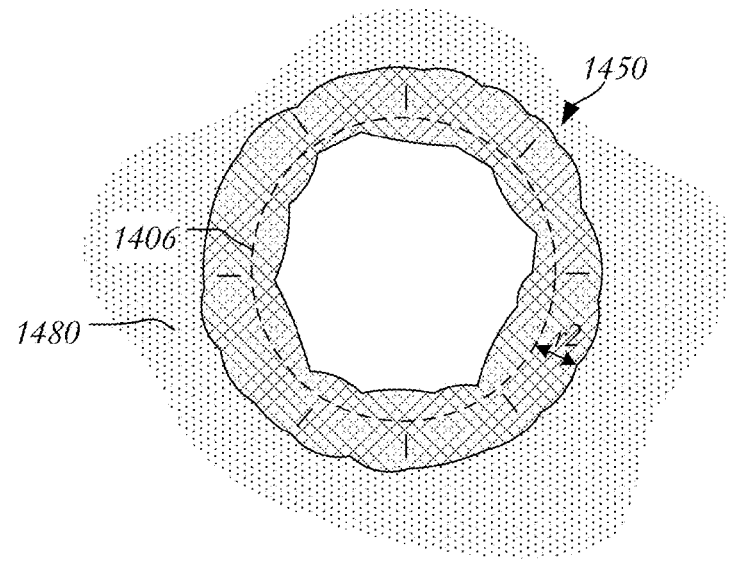
FIG. 14B is a schematic end view of the prosthetic heart valve of FIG. 14A after formation of an undulating sealing ring as seen from the annulus end toward the aortic end of the heart valve.

FIGS. 14A-B illustrates a heart valve 1400 in accordance with another embodiment. Heart valve 1400 extends between proximal end 1402 and distal end 1404, and may generally include stent 1406 formed of struts 1407, and valve assembly 1408 having a plurality of leaflets 1410 and a cuff 1412. Cuff 1412 may include a surplus portion 1422 that extends proximally past the most-proximal struts 1407 of stent 1406. In some examples, surplus portion 1422 may extend between about 5 mm and about 20 mm from the most-proximal struts 1407 of stent 1406. Surplus portion 1422 may be formed of the same material as the rest of cuff 1412 and may be integrally formed therewith of a single piece of material.

In this example, surplus portion 1422 is formed of a thickened material that is configured to circumferentially buckle in an accordion-like fashion at certain locations to form undulating sealing ring 1450 when heart valve 1400 is released from a delivery device. Undulating sealing ring 1450 allows for more surface area to fill in and around voids. Furthermore, undulating sealing ring 1450 is capable of being folded in an organized manner for loading and delivery. Terminal sutures TS1 may attach portions of surplus portion 1422 to selected struts 1407 to aid in the formation of undulating ring 1450. In some examples, sutures TS1 are the same sutured that are used to attach cuff 1412 to the struts 1407 so that no extra steps or bulk is added. Undulating ring 1450 is annularly disposed around proximal end 1402 of heart valve 1400. Undulating ring 1450 alternates between a series of peaks 1460 and valleys 1470 and radially expands to a diameter greater than the diameter of the proximal end of stent 1406. Undulating ring 1450 may include thin porcine pericardial tissue about between about 0.005 inches and about 0.007 inches in thickness or UHMWPE or PET fabric between about 0.003 inches and about 0.005 inches in thickness.

FIG. 14B illustrates prosthetic heart valve 1400 in native valve annulus 1480 after formation of undulating sealing ring 1450, as seen from proximal end 1402 (e.g., as seen from the annulus end toward the aortic end of the heart valve). Surplus portion 1422 has buckled to form undulating sealing ring 1450. The outer diameter of stent 1406 at the proximal end is indicated with a dashed-line. Undulating ring 1450 extends radially outward from the outer diameter of stent 1406 at the proximal end of heart valve 1400 by a radial distance r2. In at least some examples, radial distance r2 may be between about 1.0 mm and about 10.0 mm. Radial distance r2 may also be between about 1.0 mm and about 2.5 mm.

Figure 15A:
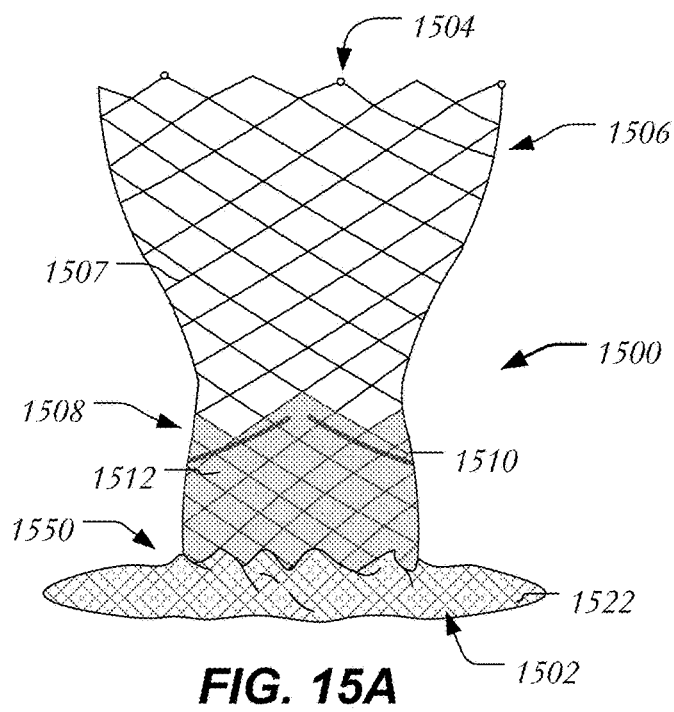
FIG. 15A is a highly schematic side view of another embodiment of a heart valve having a halo sealing ring intended to fill irregularities between the heart valve and the native valve annulus.

In another variation (FIGS. 15A and 15B), heart valve 1500 extends between proximal end 1502 and distal end 1504, and may generally include stent 1506 formed of struts 1507, and valve assembly 1508 having a plurality of leaflets 1510 and a cuff 1512. Cuff 1512 may include an extended surplus portion 1522 that extends proximally past the most-proximal struts 1507 of stent 1506. In some examples, surplus portion 1522 may extend between about 5.0 mm and about 10.0 mm from the most-proximal struts 1507 of stent 1506. Surplus portion 1522 may be formed of the same material as the rest of cuff 1512 and may be integrally formed therewith of a single piece of material.

Figure 15B:
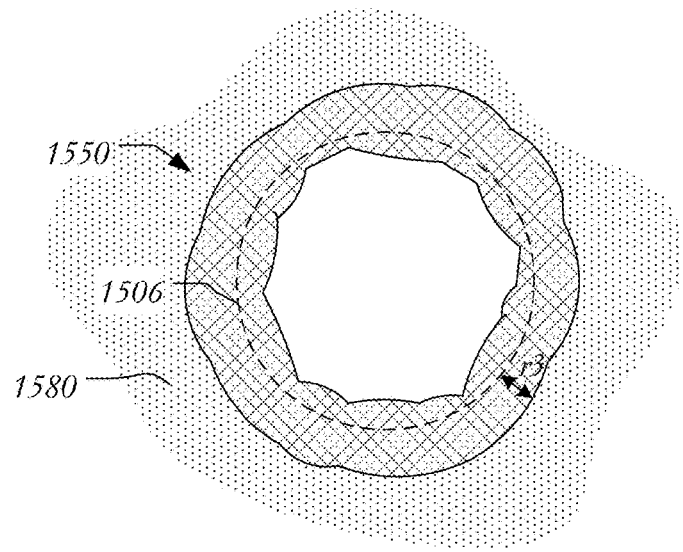
FIG. 15B is a schematic end view of the prosthetic heart valve of FIG. 15A after formation of the halo sealing ring as seen from the annulus end toward the aortic end of the heart valve.

In this example, surplus portion 1522 deploys into a flat sealing halo 1550, which flares radially outward to a diameter greater than the diameter of the proximal end of stent 1506. FIG. 15B illustrates prosthetic heart valve 1500 in native value annulus 1580 after formation of sealing halo 1550, as seen from proximal end 1502 (e.g., as seen from the annulus end toward the aortic end of the heart valve. The outer diameter of stent 1506 at the proximal end is indicated with a dashed-line. Sealing halo 1550 extends radially outward from the outer diameter of stent 1506 at the proximal end of heart valve 1500 by a radial distance r3. In at least some examples, radial distance r3 is between about 2 mm and about 10 mm.

Figure 16A:
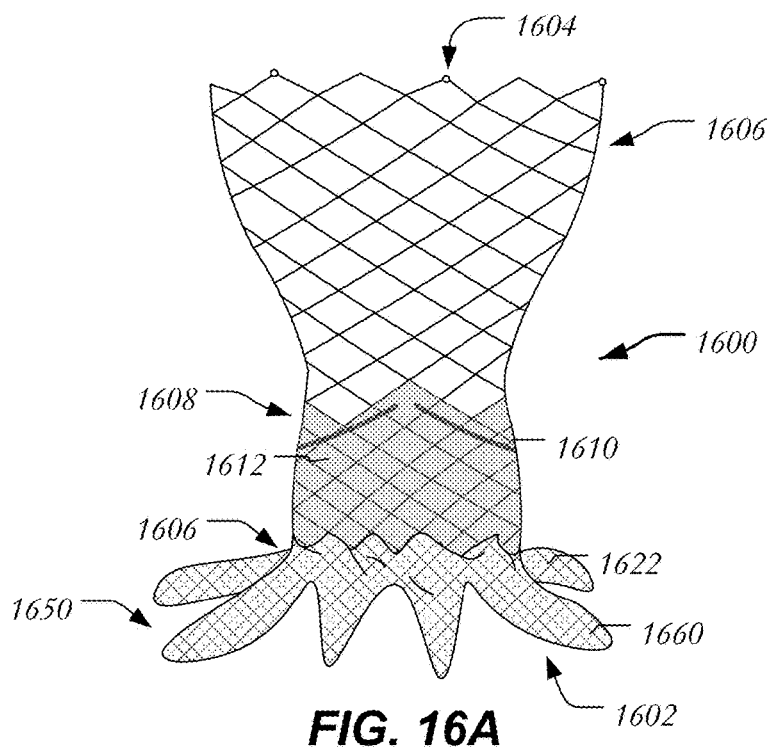
FIG. 16A is a highly schematic side view of another embodiment of a heart valve having a sealing body with limbs intended to fill irregularities between the heart valve and the native valve annulus.

In another variation (FIGS. 16A and 16B), heart valve 1600 extends between proximal end 1602 and distal end 1604, and may generally include stent 1606 formed of struts 1607, and valve assembly 1608 having a plurality of leaflets 1610 and a cuff 1612. Cuff 1612 may include an extended surplus portion 1622 that extends proximally past the most-proximal struts 1607 of stent 1606. In some examples, surplus portion 1622 may extend between about 2 mm and about 10.0 mm from the most-proximal struts 1607 of stent 1606. Surplus portion 1622 may be formed of the same material as the rest of cuff 1612 and may be integrally formed therewith of a single piece of material.

Figure 16B:
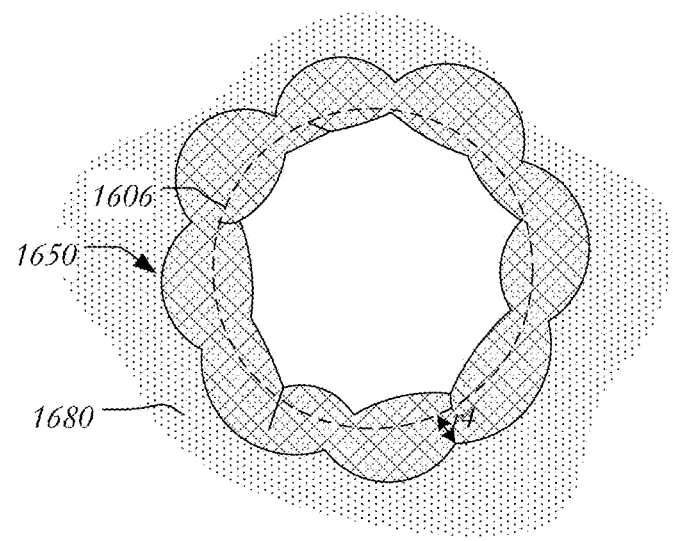
FIG. 16B is a schematic end view of the prosthetic heart valve of FIG. 16A after formation of the sealing body as seen from the annulus end toward the aortic end of the heart valve.

In this example, surplus portion 1622 forms sealing body 1650 having a number of independently moveable limbs 1660, which flare out radially. FIG. 16B illustrates prosthetic heart valve 1600 in native valve annulus 1680, as seen from proximal end 1602 (e.g., as seen from the annulus end toward the aortic end of the heart valve). Surplus portion 1622 has flared radially outward to form sealing body 1650 and limbs 1660 have also spread apart. The outer diameter of stent 1606 at the proximal end is indicated with a dashed-line. Sealing body 1650 extends radially outward from the outer diameter of stent 1606 at the proximal end of heart valve 1600 by a minimum radial distance of at least r4. In at least some examples, radial distance r4 is between about 2.0 mm and about 10.0 mm.

While the inventions herein have been described for use in connection with heart valve stents having a particular shape, the stent could have different shapes, such as a flared or conical annulus section, a less-bulbous aortic section, and the like, as well as a differently shaped transition section. The sealing rings described may also have a circular, D-shaped or elliptical cross-section. Additionally, though the sealing structures have been described in connection with expandable transcatheter aortic valve replacement, they may also be used in connection with other expandable cardiac valves, as well as with surgical valves, sutureless valves and other devices in which it is desirable to create a seal between the periphery of the device and the adjacent body tissue.

In some embodiments, a prosthetic heart valve for replacing a native valve includes a collapsible and expandable stent having a proximal end and a distal end and a valve assembly disposed within the stent, the valve assembly including a plurality of leaflets. The heart valve further includes a cuff annularly disposed about the stent and having a surplus portion capable of forming a sealing structure at the proximal end of the stent, the sealing structure having a deployed condition with a diameter in the deployed condition greater than a diameter of the proximal end of the stent.

In some examples, the surplus portion may include at least one of a metallic mesh, a shape-memory material, a polymeric material or a tissue material. The sealing structure may include a toroid formed by rolling the surplus portion upon itself. The stent may include horseshoe-shaped ends and the toroid is coupled to at least some of the horseshoe-shaped ends via a plurality of locking sutures. The plurality of locking sutures may include three locking sutures. The stent may include an annulus section and the toroid may be disposed proximal to the annulus section of the stent. The stent may include an annulus section and the toroid may be disposed about the annulus section of the stent. The sealing structure may include an undulating sealing ring having a plurality of alternating peaks and valleys. The stent may include a plurality of struts and the surplus portion is coupled to selected ones of the struts via terminal sutures to enable circumferential buckling of the surplus portion into the undulating sealing ring. The sealing structure may include a flat sealing halo. The sealing structure may include a body having a plurality of independently moveable limbs. The diameter of the sealing structure in the deployed condition may have a diameter greater than the diameter of the proximal end of the stent by between about 2.0 mm and about 10.0 mm.

In some embodiments, a prosthetic heart valve for replacing a native valve includes a collapsible and expandable stent having a proximal end and a distal end, a valve assembly disposed within the stent, the valve assembly including a plurality of leaflets and a cuff annularly disposed about the stent and having an attached end coupled to the stent and a free end extending past the proximal end of the strut and capable of forming a sealing structure for sealing gaps between the prosthetic heart valve and a native valve annulus.

In some examples, a free end is configured to roll upon itself to create a toroid. The free end may be configured to flare out radially to form a flattened halo adjacent the proximal end of the stent. The free end may include a body having a plurality of independently moveable limbs.

In some embodiments, a method of making a prosthetic heart valve for replacing a native valve includes providing a collapsible and expandable stent having a proximal end and a distal end, coupling a valve assembly to the stent, the valve assembly including a plurality of leaflets, coupling a cuff to the stent so that a surplus portion of the cuff extends beyond the proximal end of the strut and converting the surplus portion of the cuff into a sealing structure at the proximal end of the stent, the sealing structure having a diameter greater than a diameter of the proximal end of the stent.

In some examples, a converting step includes rolling the surplus portion of the cuff into a toroid shape. The method may further include securing the surplus portion to the stent via at least one suture to maintain the toroid shape.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic heart valve for replacing a native valve, comprising:
   a collapsible and expandable stent having a proximal end, a distal end, and a plurality of struts forming rows of cells, the stent in a deployed condition having a first diameter adjacent the proximal end, and a second diameter adjacent the distal end, the second diameter being greater than the first diameter;
   a valve assembly disposed within the stent, the valve assembly including:
      a plurality of leaflets, each leaflet having an attached edge and a free edge; and
      a cuff annularly disposed on a surface of the stent to cover at least one row of cells, and having an attached end coupled to the stent at a location distal to the attached edges of the plurality of leaflets; and
   a sealing ring for sealing gaps between the prosthetic heart valve and a native valve annulus, the sealing ring being formed from a braided fabric having a free end rolled over itself at least one full revolution toward the distal end of the stent so that the sealing ring is rolled around a circumferentially-extending central axis in a rolling direction, the sealing ring having an outer sealing diameter that is greater than the first diameter, but smaller than the second diameter,
   wherein the stent includes elongated legs extending away from the distal end of the stent and coupled to the sealing ring, the elongated legs extending around the circumferentially-extending central axis in the rolling direction, the elongated legs being formed of a shape memory material having a memory bias towards a rolled shape.

2. The prosthetic heart valve of claim 1, wherein the legs are curled in the sealing ring in the at least one full revolution along with the free end of the braided fabric.

3. The prosthetic heart valve of claim 1, wherein the sealing ring includes at least one of a metallic mesh, a shape-memory material, or a polymeric material.

4. The prosthetic heart valve of claim 3, wherein the sealing ring includes a braided metal fabric.

5. The prosthetic heart valve of claim 1, wherein the sealing ring comprises a toroid.

6. The prosthetic heart valve of claim 5, wherein the stent includes an annulus section and the toroid is disposed proximal to the annulus section of the stent.

7. The prosthetic heart valve of claim 1, wherein the outer sealing diameter of the sealing ring in the deployed condition is greater than the first diameter by between about 2.0 mm and about 10.0 mm.

8. A prosthetic heart valve for replacing a native valve, comprising:
   a collapsible and expandable stent having a proximal end, a distal end, and a plurality of struts forming rows of cells;
   a valve assembly disposed within the stent, the valve assembly including:

a plurality of leaflets, each leaflet having an attached edge and a free edge; and a cuff annularly disposed on a surface of the stent to cover at least one row of cells, and having an attached end coupled to the stent at a location distal to the attached edges of the plurality of leaflets; and a sealing ring for sealing gaps between the prosthetic heart valve and a native valve annulus, the sealing ring being formed of a braided fabric having a free end extending proximally of the proximal end of the stent and having a memory bias such that the free end is configured to roll over itself in a rolling direction at least one full revolution around a circumferentially-extending central axis toward the distal end of the stent, wherein the stent includes elongated legs extending away from the distal end of the stent and coupled to the sealing ring, the elongated legs being formed of a shape memory material having a memory bias towards a rolled shape in which the elongated legs curl in the rolling direction around the circumferentially-extending central axis.

9. The prosthetic heart valve of claim 8, wherein the sealing ring includes at least one of a metallic mesh, a shape-memory material, or a polymeric material.

10. The prosthetic heart valve of claim 9, wherein the sealing ring includes a braided metal fabric.

11. The prosthetic heart valve of claim 8, wherein the sealing ring comprises a toroid.

12. The prosthetic heart valve of claim 11, wherein the stent includes an annulus section and the toroid is disposed proximal to the annulus section of the stent.

13. A prosthetic heart valve for replacing a native valve, comprising:

a collapsible and expandable stent having a proximal end, a distal end, and a plurality of struts forming rows of cells, the stent being movable between collapsed and deployed conditions, the stent in a deployed condition having a first diameter adjacent the proximal end, and a second diameter adjacent the distal end, the second diameter being greater than the first diameter;

a valve assembly disposed within the stent, the valve assembly including:

a plurality of leaflets, each leaflet having an attached edge and a free edge; and a cuff annularly disposed on a surface of the stent to cover at least one row of cells, and having an attached end coupled to the stent at a location distal to the attached edges of the plurality of leaflets; and a sealing ring for sealing gaps between the prosthetic heart valve and a native valve annulus, the sealing ring being formed of a braided fabric that in the collapsed condition of the stent has a free end extending proximally of the proximal end of the stent, the braided fabric having a memory bias such that the free end is configured to roll over itself, and the braided fabric in the deployed condition of the stent having the free end rolled over itself in a rolling direction at least one full revolution around a circumferentially-extending central axis toward the distal end of the stent, the sealing ring having an outer sealing diameter that is greater than the first diameter, but smaller than the second diameter, wherein the stent includes elongated legs extending away from the distal end of the stent and coupled to the sealing ring, the elongated legs being formed of a shape memory material having a memory bias towards a rolled shape in which the elongated legs curl in the rolling direction around the circumferentially-extending central axis.

14. The prosthetic heart valve of claim 13, wherein the legs are movable between an extended configuration and a relaxed configuration in the rolled shape, the legs having the extended configuration in the collapsed condition of the stent, the legs having the relaxed configuration in the rolled shape in the deployed condition of the stent.

15. The prosthetic heart valve of claim 13, wherein the sealing ring includes at least one of a metallic mesh, a shape-memory material, or a polymeric material.

16. The prosthetic heart valve of claim 15, wherein the sealing ring includes a braided metal fabric.

17. The prosthetic heart valve of claim 13, wherein the sealing ring comprises a toroid with the braided fabric in the deployed condition.

18. The prosthetic heart valve of claim 17, wherein the stent includes an annulus section and the toroid is disposed proximal to the annulus section of the stent.

19. The prosthetic heart valve of claim 13, wherein the outer sealing diameter of the sealing ring in the deployed condition is greater than the first diameter by between about 2.0 mm and about 10.0 mm.

* * * * *